US008080523B2

(12) United States Patent
Beeton et al.

(10) Patent No.: US 8,080,523 B2
(45) Date of Patent: Dec. 20, 2011

(54) ANALOGS OF SHK TOXIN AND THEIR USES IN SELECTIVE INHIBITION OF KV1.3 POTASSIUM CHANNELS

(75) Inventors: Christine Beeton, Irvine, CA (US); George K. Chandy, Laguna Beach, CA (US); Michael William Pennington, Mount Laurel, NJ (US)

(73) Assignee: The Regents of the University of California, Oakland, CA (US)

(*) Notice: Subject to any disclaimer, the term of this patent is extended or adjusted under 35 U.S.C. 154(b) by 600 days.

(21) Appl. No.: 11/663,398

(22) PCT Filed: Oct. 7, 2005

(86) PCT No.: PCT/US2005/036234
§ 371 (c)(1),
(2), (4) Date: Aug. 16, 2007

(87) PCT Pub. No.: WO2006/042151
PCT Pub. Date: Apr. 20, 2006

(65) Prior Publication Data
US 2008/0221024 A1 Sep. 11, 2008

Related U.S. Application Data

(60) Provisional application No. 60/617,395, filed on Oct. 7, 2004.

(51) Int. Cl.
A61K 38/00 (2006.01)
A61K 38/16 (2006.01)
A61K 38/28 (2006.01)
A61P 3/04 (2006.01)
A61P 25/00 (2006.01)
A61P 3/10 (2006.01)
A61P 7/12 (2006.01)

(52) U.S. Cl. .................. 514/17.4; 514/6.9; 514/17.7
(58) Field of Classification Search ............... None
See application file for complete search history.

(56) References Cited

U.S. PATENT DOCUMENTS 6,077,680 A * 6/2000 Kem et al. ................ 435/7.24
6,616,944 B2 * 9/2003 Kissel et al. ................ 424/477
6,861,405 B2 3/2005 Desir et al.

FOREIGN PATENT DOCUMENTS
WO        9823639        6/1998

OTHER PUBLICATIONS

Pennington et al. Structural Stabilization and Minimization of the Potassium Channel Blocker, ShK Toxin. Peptides 2000, pp. 155-156.*
Beeton et al. A Novel Fluorescent Toxin to Detect and Investigate Kv1.3 Channel Up-regulation in Chronically Activated T Lymphocytes. The Journal of Biological Chemistry. vol. 278, No. 11, Issue of Mar. 14, 2003. Published JBC Papers in Press, Jan. 2, 2003, pp. 9928-9937.*
Hruby. Designing Peptide Receptor Agonists and Antagonists. Nature Reviews. Drug Discovery. Nov. 2002. vol. 1, pp. 847-858.*
H.J.C. Berendsen. A Glimpse of the Holy Grail? Science (1998) 282, pp. 642-643.*
Rudinger. In: Peptide Hormones, JA Parsons, Ed. (1976), pp. 1-7.*
SIGMA. Designing Custom Peptides. http://www.sigma-genosys.com/peptide_design.asp (Accessed Dec. 16, 2004), 2 pages.*
W.S. Messer, "Vasopressin and Oxytocin", web document updated Apr. 3, 2000; http://www.neurosci.pharm.utoledo.edu/MBC3320/vasopressin.htm; 5 pages.*
D.E. Smilek, et al. Proc. Natl. Acad. Sci. USA (1991) 88, pp. 9633-9637.*
D. Voet and J.G. Voet. Biochemistry, 2nd Edition.(1995), pp. 235-241.*
Beeton et al. Targeting Effector Memory T Cells with a Selective Peptide Inhibitor of Kv1.3 Channels for Therapy of Autoimmune Diseases. Molecular Pharmacology, 2005. vol. 67, No. 4, pp. 1369-1381.*
Beeton, C et al., Selective blockage of T lymphocyte K+ channels ameliorates experimental autoimmune encephalomyelitis experimental autoimmune encephalomyelitis, a model for multiple sclerosis, Proceedings of the National Academy of Sciences of USA, Nov. 20, 2001, pp. 13942-13947, vol. 98, No. 24, Washington, DC, US.
European Search Report in reference to PA 6031 PCT/EP, European Patent Office, Sep. 10, 2009, Munich.
George, C., K+ channels as targets for specific immunomodulation, Trends in Pharmacological Sciences, May 1, 2004, pp. 280-289, vol. 25, No. 5, Elsevier, Haywarth, GB.
Kalman, et al., ShK-Dap22, a Potent Kv1.3-specific Immunosuppressive Polypeptide, J. Biol Chem., 1998, vol. 273, No. 49, pp. 32697-32707.
Lanigan, M.D. et al., Designed Peptide Analogues of the Potassium Channel Blocker ShK Toxin; Biochemistry, 25; 40 (51):15528-37, Dec. 2001.
King D.S., et al, 1990, Int. J. Peptide Protein Res., 36, 255-266.
Pennington, et al., Int. J Peptide Protein Res., 46, 354-358, 1995.

(Continued)

*Primary Examiner* — Marcela M Cordero Garcia
(74) *Attorney, Agent, or Firm* — Robert D. Buyan; Stout, Uxa, Buyan & Mullins

(57) ABSTRACT

Analogs of ShK toxin and methods for using such ShK analogs. The ShK analogs generally comprise ShK toxin attached to a chemical entity (e.g. an atom, molecule, group, residue, compound, moiety, etc.) that has an anionic charge. In some embodiments the chemical entity attached to the ShK toxin may comprise an amino acid residue. The ShK analogs may be administered to human or non-human animal subjects to cause inhibition of potassium channels or to otherwise treat diseases or disorders. In some embodiments, the chemical entity to which the ShK toxin is attached may be chosen to provide selective inhibition of certain potassium channels (e.g., Kv1.3 channels) over other potassium channels (e.g., Kv1.1 channels). In come embodiments, the chemical entity to which the ShK toxin is attached may include a fluorophore, thereby providing a fluorophore tagged ShK analog. Such fluorophore tagged ShK analogs may be used in flow cytometry alone, or in conjunction with class II tetramers that can detect autoreactive cells.

40 Claims, 20 Drawing Sheets

OTHER PUBLICATIONS

Stewart, J.M., et al., Solid Phase Peptide Sythesis, 2nd Edition, Pierce Chemical Company, Rockford, Ill., 1984.
Wilken, J. et al., Chemical Protein Synthesis, Current Opin. Biotech., 9, 412-426, 1998.
Albericio, F., Convergent Peptide Synthesis; in Methods in Enzymol. Ed G. Fields, Academic Press, New York, NY, pp. 313-335, Available online Dec. 8, 2003.
Beeton, C. et al., Targeting Effector Memory T Cells with a Selection Peptide Inhibitor of Kv1.3 Channels for Therapy of Autoimmune Diseases, Molecular Pharmacology, vol. 67, No. 4, 1369-, 2005.
Beeton, C. et al., A Novel Fluorescent Toxin to Detect and Investigate Kv1.3 Channel Up-Regulation in Chronically Activated T Lymhocytes, J. Biol. Chem., vol. 278, No. 11, 9928-9937, Mar. 2003.

* cited by examiner

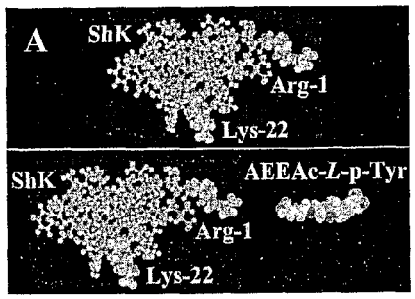

Fig. 2A

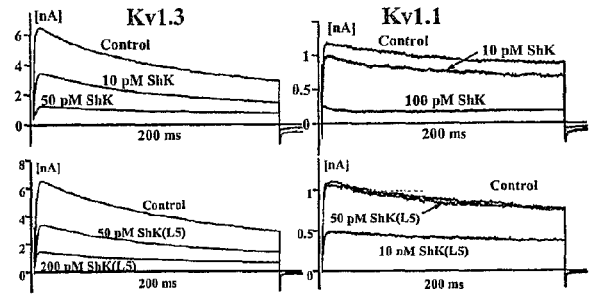

Fig. 2B

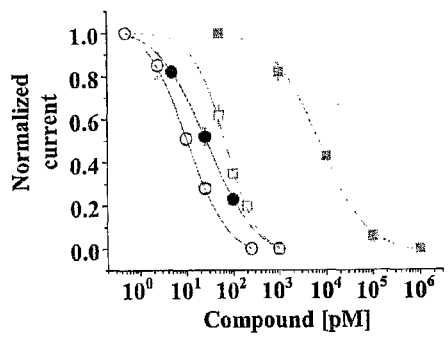

Fig. 2C

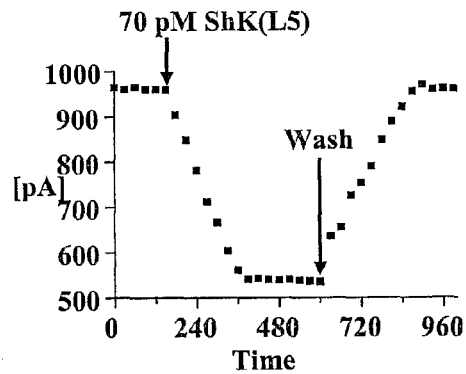

Fig. 2D

| Compound | Residue attached at position -2 | Net charge at position -2 | $K_d$ on Kv1.3 [pM] | $K_d$ on Kv1.1 [pM] | Ratio of $K_d$s |
|---|---|---|---|---|---|
| ShK | None | None | 10 ± 1 | 28 ± 6 | 2.8 |
| ShK(L5) | L-p-Tyr | -2 | 69 ± 5 | 7,400 ± 900 | 104.2 |
| ShK(D5) | D-p-Tyr | -2 | 1,100 ± 150 | 39,000 ± 650 | 35.4 |
| ShK(L6) | L-p-Tyr monomethyl | -1 | 10 ± 1 | 112 ± 9 | 11.2 |
| ShK(L7) | L-p-Tyr dimethyl | 0 | 24 ± 2 | 175 ± 30 | 7.3 |
| ShK(L4) | L-Tyr | 0 | 47 ± 6 | 159 ± 5 | 3.4 |
| ShK(L1) | L-Pmp | -2 | 293 ± 45 | 1,000 ± 100 | 3.4 |
| ShK(D1) | D-Pmp | -2 | 96 ± 12 | 1,400 ± 80 | 14.6 |
| ShK(D2) | D-Pmp monoethyl | -1 | 311 ± 16 | 1,100 ± 100 | 3.5 |
| ShK(L3) | L-Pmp diethyl | 0 | 71 ± 6 | 1,100 ± 200 | 15.5 |
| ShK(D3) | D-Pmp diethyl | 0 | 70 ± 9 | 166 ± 13 | 2.4 |
| ShK(L9) | L-p-COOH-Phe | -1 | 94 ± 7 | 319 ± 36 | 3.4 |
| ShK-L8 | L-p-amino-Phe | +1 | 65 ± 4 | 142 ± 13 | 2.2 |
| ShK-F6CA | F6CA | -1 | 48 ± 4 | 4,000 ± 300 | 83 |
| ShK-Dap$^{22}$ | None | None | 52 ± 3 | 1,800 ± 577 | 35 |

Fig. 2E

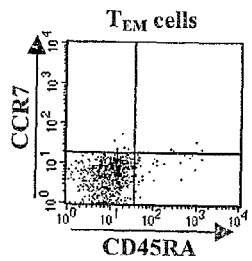
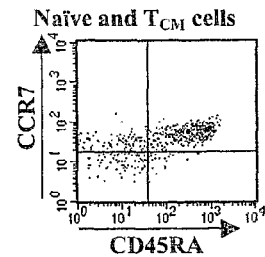
Fig. 3A
Fig. 3B
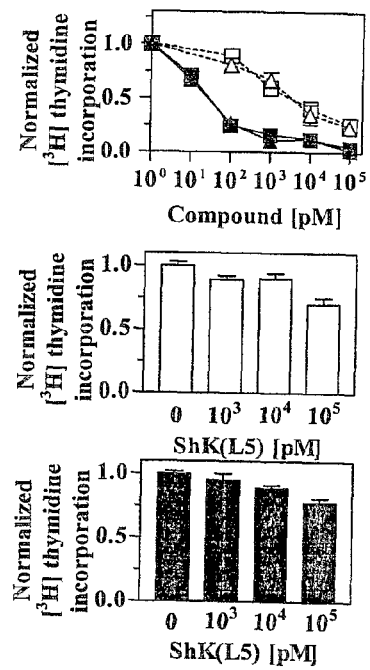
Fig. 3C
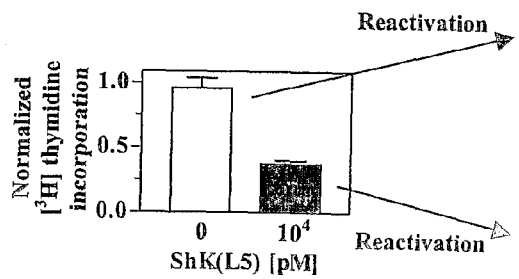
Fig. 3D

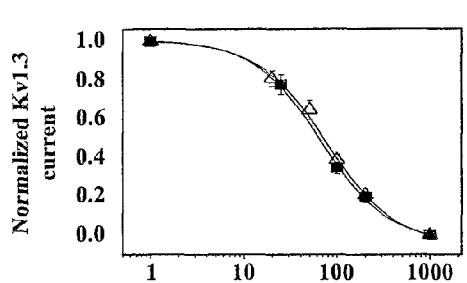 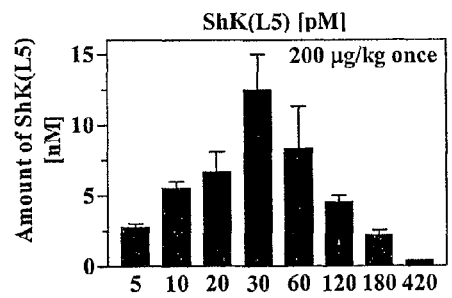
*Fig. 5A*  *Fig. 5B*
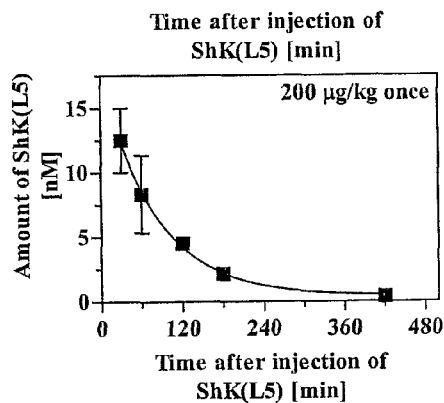 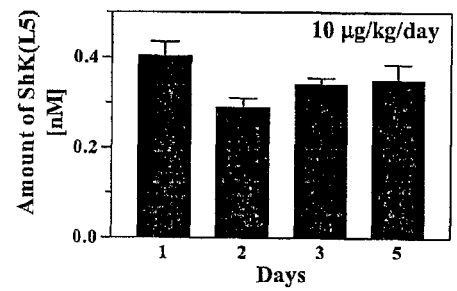
*Fig. 5C*  *Fig. 5D*
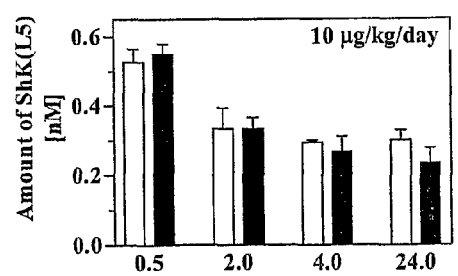 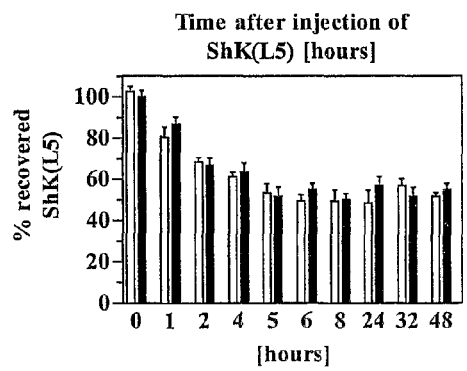
*Fig. 5E*  *Fig. 5F*

APC loaded with GAD557I and DAPI

APC loaded with GAD557I and DAPI
No contact between T and B cells

APC loaded with MBP and DAPI

APC loaded with GAD557I and DAPI
ShK(L5) does not prevent IS formation

APC loaded with GAD557I and DAPI
ShK(L5) does not disrupt the IS

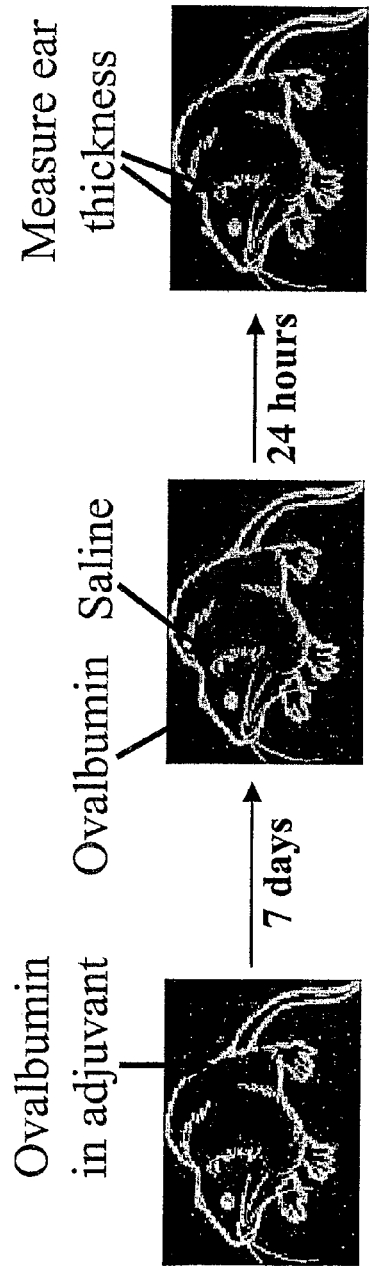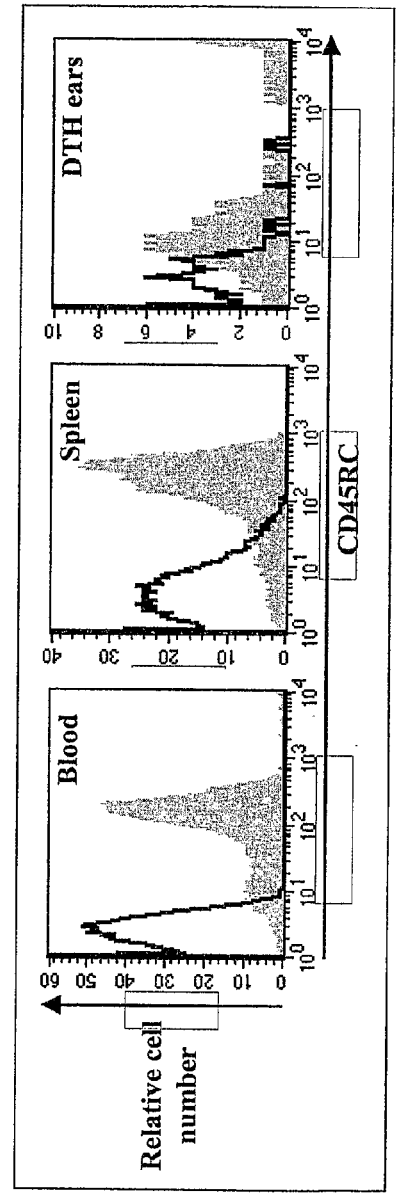
Fig. 9

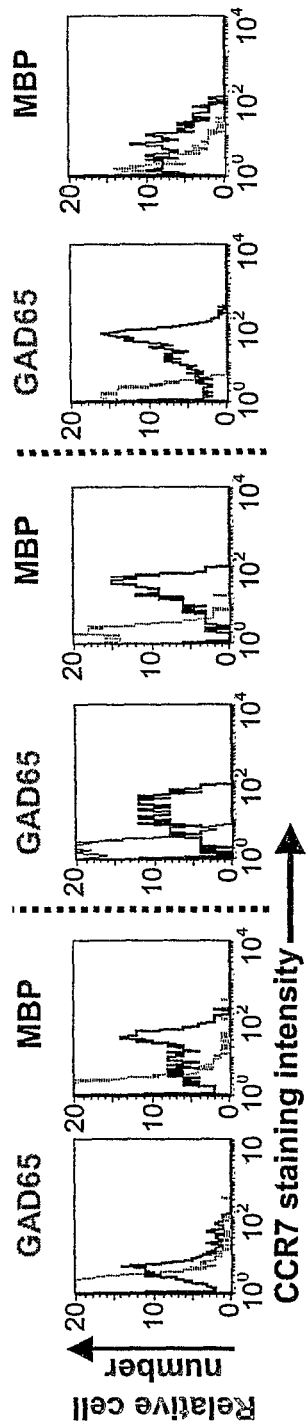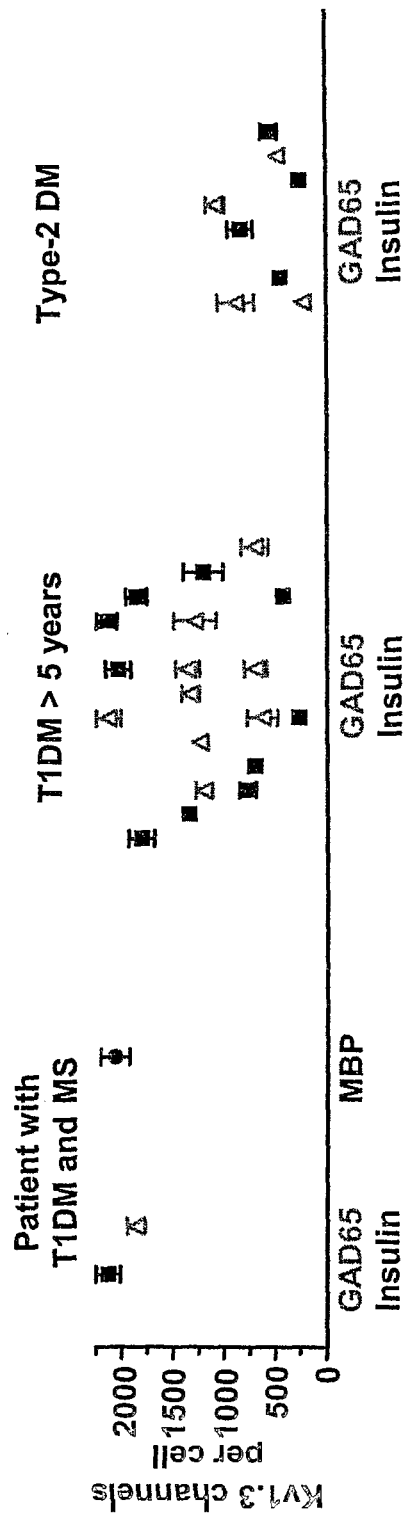
Fig. 12C
Fig. 12D

US 8,080,523 B2

ANALOGS OF SHK TOXIN AND THEIR USES IN SELECTIVE INHIBITION OF KV1.3 POTASSIUM CHANNELS

RELATED APPLICATION

This patent application claims priority to U.S. Provisional Patent Application No. 60/617,395 filed on Oct. 7, 2004, the entirety of which is expressly incorporated herein by reference.

SEQUENCE LISTING

The instant application contains a Sequence Listing which has been submitted in ASCII format via EFS-Web and is hereby incorporated by reference in its entirety. Said ASCII copy, created on Aug. 15, 2011, is named UCIVN66U.txt and is 2,638 bytes in size.

FIELD OF THE INVENTION

The present invention provides a) novel compositions of matter, b) methods and kits for in vivo and/or in vitro inhibition of the Kv1.3 channel in T- and B-lymphocytes and other cell types and c) methods for treating autoimmune and other disorders in human or animal subjects.

BACKGROUND OF THE INVENTION

Cell plasma membranes form the outer surfaces of eukaryotic cells. Various ions (e.g., sodium, potassium, calcium, etc.) move in and out of cells by passive diffusion through the cells' plasma membranes. Such diffusion of ions into and out of cells is facilitated by the presence of "ion channels" within the cell membranes. Ion channels are proteins embedded within the cell membrane that control the selective flux of ions across the membrane, thereby allowing for the formation of concentration gradients between the intracellular contents of the cell and the surrounding extracellular fluid. Because ion concentrations are directly involved in the electrical activity of excitable cells (e.g., neurons), the functioning (or malfunctioning) of ion channels can substantially control the electrical properties and behavior of such cells. Indeed, a variety of disorders, broadly termed "channelopathies," are believed to be linked to ion channel insufficiencies or dysfunctions.

Ion channels are referred to as "gated" if they can be opened or closed. The basic types of gated ion channels include a) ligand gated channels, b) mechanically gated channels and c) voltage gated channels. In particular, voltage gated channels are found in neurons, muscle cells and non-excitable cells such as lymphocytes. They open or close in response to changes in the charge across the plasma membrane.

Kv1.3 Channels and Autoimmune Diseases.

Autoimmune diseases such as multiple sclerosis (MS), type-1 diabetes mellitus (T1DM), rheumatoid arthritis (RA) and psoriasis affect several hundred million people worldwide. In these disorders specific autoreactive T cells—for instance myelin-specific T cells in MS patients—are believed to undergo repeated autoantigen stimulation during the course of disease and differentiate into chronically activated memory cells that contribute to pathogenesis by migrating to inflamed tissues and secreting cytokines (Viglietta et al., 2002; Vissers et al., 1002; Wulff et al., 2003b). Therapies that preferentially target chronically activated memory T cells would have significant value for autoimmune diseases.

Memory T cells are divided into two subsets—central memory ($T_{CM}$) and effector memory ($T_{EM}$)—based on the expression of the chemokine receptor CCR7 and the phosphatase CD45RA (Geginat et al., 2001; Sallusto et al., 1999). Naïve and $T_{CM}$ cells home to the lymph node before they migrate to sites of inflammation, whereas $T_{EM}$ cells home directly to sites of inflammation where they secrete copious amounts of IFN-β and TNF-α and exhibit immediate effector function. It has recently been shown that myelin-specific autoreactive T cells in MS patients are predominantly activated $T_{EM}$ cells (Wulff et al., 2003b), and adoptive transfer of myelin-specific activated rat $T_{EM}$ cells into naïve recipients induced severe EAE (Beeton et al., 2001a; Beeton et al., 2001b). An exciting new therapeutic target for immunomodulation of $T_{EM}$ cells is the voltage-gated Kv1.3 K$^+$ channel. $T_{EM}$ cells up-regulate Kv1.3 channels upon activation and their antigen-driven proliferation is exquisitely sensitive to Kv1.3 blockers (Wulff et al., 2003b). Naïve and $T_{CM}$ cells in contrast are significantly less sensitive to Kv1.3 blockers to begin with and rapidly become resistant to Kv1.3 blockade by up-regulating the calcium-activated K$^+$ channel IKCa1 (Ghanshani et al., 2000; Wulff et al., 2003b).

The dominance of Kv1.3 in $T_{EM}$ cells provides a powerful way to manipulate the activity of this subset with specific Kv1.3 inhibitors. The functionally restricted tissue distribution of the channel and the fact that in vivo Kv1.3 blockade ameliorates $T_{EM}$-mediated EAE, bone resorption in peridontal disease and delayed type hypersensitivity reactions in animal models without causing obvious side effects has enhanced the attractiveness of Kv1.3 as a therapeutic target (Beeton et al., 2001b; Koo et al., 1997; Valverde et al., 2004). Although Kv1.3 blockers would suppress all activated $T_{EM}$ cells (for example $T_{EM}$ cells specific for vaccine antigens), a Kv1.3-based therapy would be a significant improvement over current therapies that broadly and indiscriminately modulate the entire immune system. An additional advantage of Kv1.3 blockers is that they are reversible. Thus, one could titrate the therapeutic effect of Kv1.3 blockers when needed and stop therapy in the face of infection, unlike chemotherapeutic agents, which take months to subside.

Kv1.3 Channels and Obesity

The Kv1.3 channel was found to play a role in energy homeostasis and energy balance (*Hum Mol Genet.* 2003 12:551-9). Mice with the Kv1.3 channel genetically knocked out were able to eat fatty diets without gaining weight, while control mice given the same diet became over-weight. Pharmacological blockade of Kv1.3 channels recapitulated the effect of genetic knockout of Kv1.3 channels. Consequently, Kv1.3 blockers are likely to have use in the management of obesity.

Kv1.3 Channels and Type-2 Diabetes Mellitus.

Kv1.3 channels play a role in regulating insulin-sensitivity in peripheral target organs such as the liver and muscle (*Proc Natl Acad Sci USA.* 2004 101:3112-7). Genetic knockout of the Kv1.3 channel in mice enhanced the sensitivity of the liver and muscle to insulin. Consequently, Kv1.3 blockers may have use in the treatment of type-2 diabetes mellitus by enhancing insulin's peripheral actions and thereby decreasing blood glucose levels.

Naturally Occurring Polypeptides Known to Inhibit Kv1.3 Channels

The most potent Kv1.3 inhibitor is the peptide ShK from the Caribbean sea anemone *Stichodactyla helianthus*. ShK is a 35-residue polypeptide cross-linked by 3 disulfide bridges. ShK blocks Kv1.3 ($K_d$=11 pM) and suppresses proliferation of $T_{EM}$ cells at picomolar concentrations, and ameliorates experimental autoimmune encephalomyelitis (EAE) in rats induced by the adoptive transfer of myelin-specific $T_{EM}$ cells. A potential drawback of ShK is its low picomolar affinity for the neuronal Kv1.1 channel ($K_d$ 28 pM). Although no side effects were observed with ShK in EAE trials, ingress of high concentrations of ShK into the brain, as might happen when the blood-brain-barrier is compromised in MS, could lead to unwanted neurotoxicity. The development of highly specific Kv1.3 inhibitors is therefore necessary. An extensive effort by the pharmaceutical industry and academic groups has yielded several small molecules that inhibit Kv1.3 in the mid-nanomolar range, but these compounds do not have the selectivity or potency to make them viable drug candidates.

Several truncated peptidic analogs of ShK have previously been reported. In one of these ShK analogs, the native sequence was truncated and then stabilized by the introduction of additional covalent links (a non-native disulfide and two lactam bridges). In others, non-native structural scaffolds stabilized by disulfide and/or lactam bridges were modified to include key amino acid residues from the native toxin. These ShK analogs exhibited varying degrees of Kv1.3 inhibitory activity and specificity. Lanigan, M. D. et al.; Designed Peptide Analogues of the *Potassium Channel Blocker ShK Toxin*; Biochemistry, 25; 40(51):15528-37 (December 2001).

There remains a need in the art for the development of new analogs of ShK that selectively inhibit Kv1.3 channels in lymphocytes with minimal or no inhibitory effects on Kv1.1 channels or other potassium channels.

SUMMARY OF THE INVENTION

The present invention provides novel compositions (referred to herein as "ShK analogs") comprising ShK toxin attached (e.g., bound, linked by a linker or otherwise associated with) to an organic or inorganic chemical entity (e.g. an atom, molecule, group, residue, compound, moiety, etc.) that has an anionic charge.

Further in accordance with the present invention, there are provided methods for inhibiting potassium channels and/or treating diseases or disorders in human or animal subjects by administering to the subject an effective amount of an ShK analog of the present invention. In some embodiments, the chemical entity to which the ShK toxin is attached may be chosen to provide selective inhibition of certain potassium channels (e.g., Kv1.3 channels) over other potassium channels (e.g., Kv1.1 channels).

Still further in accordance with the present invention, ShK analogs of the foregoing character may include a fluorophore tag and such fluorophore tagged ShK analogs of the present invention may be used in flow cytometry alone, or in conjunction with class II tetramers that can detect autoreactive cells.

The known amino acid sequence of SHK toxin is Arg-Ser-Cys-Ile-Asp-Thr-Ile-Pro-Lys-Ser-Arg-Cys-Thr-Ala-Phe-Gln-Cys-Lys-His-Ser-Met-Lys-Tyr-Arg-Leu-Ser-Phe-Cys-Arg-Lys-Thr-Cys-Gly-Thr-Cys (SEQ ID NO:1). Compositions of the present invention include those having the following sequences:

p-phospho-Tyr-AEEAc-Arg-Ser-Cys-Ile-Asp-Thr-Ile-Pro-Lys-Ser-Arg-Cys-Thr-Ala-Phe-Gln-Cys-Lys-His-Ser-Met-Lys-Tyr-Arg-Leu-Ser-Phe-Cys-Arg-Lys-Thr-Cys-Gly-Thr-Cys (SEQ ID NO:2);

p-phospho-Tyr-AEEAc-Arg Ser-Cys-Ile-Asp-Thr-Ile-Pro-Lys-Ser-Arg-Ala-Phe-Gln-Cys-Lys-His-Ser-Met-Lys-Tyr-Arg-Leu-Ser-Phe-Cys-Arg-Lys-Thr-Cys-Gly-Thr-Cys-amide (SEQ ID NO:3);

Tyr-AEEAc-Arg-Ser-Cys-Ile-Asp-Thr-Ile-Pro-Lys-Ser-Arg-Cys-Thr-Ala-Phe-Gln-Cys-Lys-His-Ser-Met-Lys-Tyr-Arg-Leu-Ser-Phe-Cys-Arg-Lys-Thr-Cys-Gly-Thr-Cys-amide (SEQ ID NO:4).

Further aspects, elements and details of the present invention will be apparent to those of skill in the art upon reading the detailed description and examples set forth herebelow.

BRIEF DESCRIPTION OF THE DRAWINGS

FIG. 2A shows a molecular model of ShK based on the published NMR structure wherein the Lys[22], critical for channel blockade, is highlighted in one shade of grey. L-pTyr was attached to the α-amino group of Arg[1] of ShK (highlighted in a second shade of grey) through an Aeea linker (right). The structures of the linker and L-pTyr were modeled with AM1 in Hyperchem.

FIG. 2B shows the effect of ShK (top) and ShK (L5) (bottom) on Kv1.3 and Kv1.1 currents in stably transfected cells.

FIG. 2C shows dose-dependent inhibition of Kv1.3 (open symbols) and Kv1.1 (closed symbols) by ShK (dark) and ShK(L5) (light). $K_d$s on Kv1.3=10±1 pM (ShK) and 69±5 pM (ShK(L5)); $K_d$s on Kv1.1=28±6 pM (ShK) and 7.4±0.8 nM (ShK(L5)).

FIG. 2D shows the time course of wash-in and wash-out of ShK(L5) on Kv1.3 wherein cells were held at a holding potential of 80 mV and depolarized for 200 msec to 40 mV every 30 secs.

FIG. 2E shows $K_d$ values for inhibition of Kv1.3 and Kv1.1 by ShK analogs. $K_d$s for ShK-F6CA and ShK-Dap[22] based on published sources.

FIG. 3A is a graph showing staining intensities of CD45RA and CCR7 as determined by flow cytometry in the CD3+-gated population of human PBMCs stained with antibodies against CD3, CD45RA and CCR7.

FIG. 3B is a graph showing staining intensities of CD45RA and CCR7 as determined by flow cytometry in the CD3+-gated population in cells of a human $T_{EM}$ line stained with antibodies against CD3, CD45RA and CCR7.

FIG. 3C is a graph showing the inhibitory effects of ShK (dark grey) and ShK(L5) (light grey) of [³H] thymidine incorporation by PBMCs (open symbols, a mixture of naïve/$T_{CM}$ cells) and $T_{EM}$ cells (closed symbols) stimulated for 48 hours with anti-CD3 antibody.

FIG. 3D is a graphic showing of pre-activated human PBMCs (naïve/$T_{CM}$ cells) that up-regulate KCa3.1 expression become resistant to ShK(L5) inhibition when reactivated with anti-CD3 antibody. These cells have previously been reported to become sensitive to the $K_{Ca}3.1$-specific inhibitor TRAM-34.

FIG. 5A is a graph showing Kv1.3 blocking activity of ShK(L5) as determined on Kv1.3 channels stably expressed in L929 cells.

FIG. 5B is a graph showing blood levels of ShK(L5) at various times after a single subcutaneous injection of 200 mg/kg of ShK(L5) in four rats. Blood was drawn at the indicated times and serum was tested by patch-clamp to determine the amount of ShK(L5).

FIG. 5C is a graph of the data of FIG. 5B fitted to a single exponential decay indicating a half-life of approximately 50 minutes.

FIG. 5D is a graph showing blood levels of ShK(L5) in five Lewis rats receiving single daily subcutaneous injections of 10 μg/kg/day ShK(L5) for 5 days. Blood was drawn each morning (24 hours after the previous injection) and tested for blocking activity on Kv1.3 channels by patch-clamp.

FIG. 5E is a graph showing serum levels of ShK(L5) in rats at various times following a single dose of 10 mg/kg ShK(L5) either subcutaneously (open bars; n=4) or intravenously (closed bars; n=4). Blood was drawn at the indicated times and serum was tested by patch-clamp to determine the amount of ShK(L5) in blood. ShK(L5) maintained a steady-state level of 300 pM in the blood almost 24 hours after a single subcutaneous injection. This concentration is sufficient to selectively inhibit the function of $T_{EM}$ cells.

FIG. 5F is a graph showing the % recovery of ShK(L5) after a half-blocking dose of ShK(L5) was added to rat plasma or PBS containing 2% rat plasma and incubated at 37° C. for varying duration. Aliquots were taken at the indicated times and blocking activity determined on Kv1.3 channels. ShK(L5) is extremely stable in plasma.

FIG. 9 is a diagram representing a rat model of delayed type hypersensitivity (DTH) caused by effector memory T cells.

FIG. 12C shows graphs of relative cell number vs. CCR7 staining intensity. Cells expressing high levels of Kv1.3 are CCR7-negative i.e. they are $T_{EM}$-effectors. Cells expressing low levels of Kv1.3 are CCR&-positive i.e. they are either naïve or $T_{CM}$ cells FIG. 12D shows Kv1.3 number/cell in autoreactive T cells from a patient having T1DM and MS (left), patients having T1DM for greater than 5 years duration (middle) and patients having non-autoimmune type-2 DM.

DETAILED DESCRIPTION

The following detailed description and the accompanying drawings are intended to describe some, but not necessarily all, examples or embodiments of the invention only. This detailed description and the accompanying drawings do not limit the scope of the invention in any way.

The present invention provides novel analogs of ShK, methods for making such compositions and methods for using such compositions to inhibit Kv1.3 channels (or other ion channels) in human or animal cells and for treatment or prevention of diseases and disorders, such as T cell mediated autoimmune disorders. The compositions of the present invention comprise ShK toxin attached (e.g., bound, linked by a linker or otherwise associated with) to an organic or inorganic, anionic-charged chemical entity (e.g. an atom, molecule, group, residue, compound, moiety, etc.). In at least some embodiments of the invention, the organic or inorganic, anionic-charged chemical entity may be selected to increase or optimize the affinity of the composition for inhibition of Kv1.3 channels over Kv1.1 channels. Examples of organic or inorganic, anionic-charged molecules or groups that may be linked or bound to ShK in accordance with the present invention include but are not necessarily limited to:

amino acids;
polypeptides;
amino acid residues;
unnatural amino acid residues;
threonine;
threonine derivatives;
phospho-threonine;
serine;
serine derivatives;
phospho-serine;
glutamic acid;
glutamic acid derivatives;
gammacarboxy-glutamic acid;
aspartic acid;
aspartic acid derivatives;
inorganic compounds or groups;
organic compounds or groups;
succinic anhydride; and
phthalic anhydride.

Figure 1:
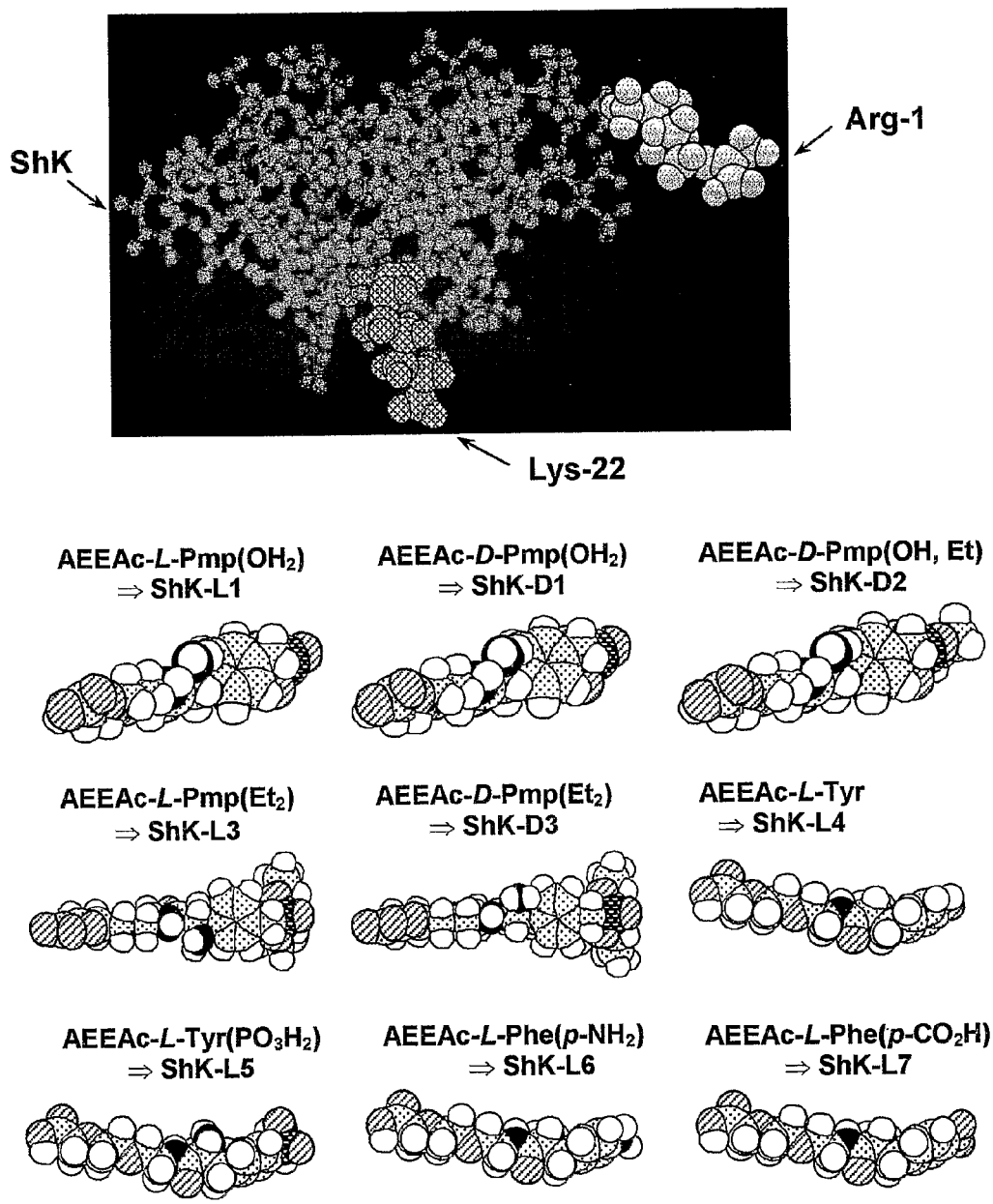
FIG. 1 shows the chemical structures of a number of ShK analogs of the present invention.

In accordance with the present invention, some non-limiting examples of compositions of the present invention, wherein the anionic-charged chemical entity comprises an amino acid residue, are shown in FIGS. 1 and 2C and referred to herein by alphanumeric designations, as shown in Table 1 below:

TABLE 1

| DESIGNATION | AMINO ACID RESIDUE BOUND TO ShK AT POSITION 2 |
|---|---|
| ShK-L1 | AEEAc-L-Pmp(OH$_2$) |
| ShK-D1 | AEEAc-D-Pmp(O$_2$) |
| ShK-D2 | AEEAc-D-Pmp(OH, Et) |
| ShK-L3 | AEEAc-L-Pmp(Et$_2$) |
| ShK-D3 | AEEAc-D-Pmp(Et$_2$) |
| ShK-L4 | AEEAc-L-Tyr |
| ShK-L5 | AEEAc-L-Tyr(PO$_3$H$_2$) |
| ShK-L6 | AEEAc-L-Phe(p-NH$_2$) |
| ShK-L7 | AEEAc-L-Phe(p-CO$_2$H) |

With specific reference to FIG. 1, tyrosine or phenylalanine or their charged non-natural derivatives were conjugated to ShK (top left) through a linker attached on its N terminus (residue Arg1 shown in shaded grey). The Lys22, required for channel blockade, is shown in a darker shade of grey. The molecular model of ShK is based on the published NMR structure and the structures of the linker and the new residues were modeled. These embodiments of compositions of the present invention generally comprise the ShK toxin, which is a polypeptide, bound to (e.g., chemically bound, linked or otherwise associated with) at least one anionic-charged amino acid residue. In embodiments where the amino acid residue has a chiral center, the D and/or L enantiomer of such amino acid residue may be used. The anionic-charged amino acid residue may be an unnatural residue and may be attached or linked to an N-terminus of the ShK polypeptide. In some embodiments, the anionic-charged amino acid residue may be linked to an N terminus of ShK through a linker, such as an aminoethyloxyethyloxy-acetyl linker. These analogs of ShK inhibit the Kv1.3 channel more specifically than ShK because they have reduced affinity for other potassium channels (e.g., Kv1.1). The ShK may be isolated from natural sources as known in the art, or it may be synthesized.

Synthesis of ShK Toxin

ShK Toxin may be synthesized by any suitable method. In one such method, Fmoc-amino acids (Bachem Feinchemikalien) including Arg(Pmc), Asp(OtBu), Cys(Trt), Gln(Trt), His(Trt), Lys(Boc), Ser(tBu) and Thr(tBu) are obtained commercially and assembled to form ShK Toxin. Stepwise assembly of the amino acids may be carried out on an Applied Biosystems 431A peptide synthesizer at the 0.25 mmol scale starting with Fmoc-Cys(Trt)-R. Residues 34 through 22 are single coupled. Thereafter, an aliquot (e.g., half) of the resin is removed to effect better mixing. The remainder of the peptide sequence is then double coupled to the remaining resin aliquot. All couplings are mediated by dicyclohexylcarbodiimide in the presence of 2 eq of 1-hydroxybenzotriazole. The final two residues are also coupled via HBTU/DIEA chemistry. These residues are Aeea (Fmoc-aminoethyloxyethyloxyacetic acid) and as the N-terminal residue Fmoc-Tyr (PO4) monobenzyl ester. Following final removal of the Fmoc-group, the peptide resin (2.42 g) is cleaved from the resin and simultaneously deprotected using reagent K for 2 h at room temperature. Reagent K is known in the art and has been described in the literature. See, King, D. S., Fields, C. G. and Fields, G. B. (1990) *Int. J. Peptide Protein Res.* 36, 255-266. Following cleavage, the peptide is filtered to remove the spent resin beads and precipitated with ice cold diethyl ether. The peptide is then collected on a fine filter funnel, washed with ice cold ether and finally extracted with 20% AcOH in H$_2$O. The peptide extract is subsequently diluted into 2 liters of H$_2$O, the pH is adjusted to 8.0 with NH$_4$OH and allowed to air oxidize at room temperature for 36 hours. Following oxidation of the disulfide bonds with a 2:1 ratio of reduced to oxidized glutathione, the peptide solution is acidified to pH 2.5 and pumped onto a Rainin Dynamax C$_{18}$ column (5.0×30 cm). The sample is eluted with a linear gradient from 5-30% acetonitrile into H$_2$O containing 0.1% TFA. The resulting fractions are analyzed using two analytical RP-HPLC systems: TFA and TEAP. Pure fractions are pooled and lyophilized. (See, Pennington, M. W., Byrnes, M. E., Zaydenberg, I., Khaytin, I., de Chastonay, J., Krafte, D., Hill, R., Mahnir, V., Volberg, W. A., Gorczyca, W. and Kem, W. R. (1995) *Int. J. Peptide Protein Res.* 46, 354-358.)

Alternatively, solid-phase peptide synthesis employing a Boc-Bzl protecting group strategy may be utilized to assemble the primary structure as well as analogs of the peptide. The peptide could then be cleaved from the solid-phase by anhydrous HF, yielding the linear peptide ready for folding as described above for the Fmoc synthesized peptide. (See, Stewart, J. M. and Young J. D. (1984) Solid Phase Peptide Synthesis. 2$^{nd}$ Edition. Pierce Chemical Company. Rockford, Ill.)

Alternatively, other synthetic methods to assemble the primary structure of ShK or analogs could include chemical ligation technology where the peptide is prepared as a series of designed fragments with C-terminal thioester peptides. The thioester peptide can react with another peptide containing an N-terminal Cys residue to form a peptide containing a native peptide bond. By using this technology, one could effectively assemble the primary structure of ShK. (See, (4) Wilken, J. and Kent S. B. H. (1998) Chemical protein synthesis. *Current Opin. Biotech.* 9, 412-426.)

Alternatively, another synthetic method that may be employed to assemble the primary structure of ShK would utilize a protected peptide fragment convergent approach as described in Albericio, F., Lloyd-Williams, P., and Giralt, E. (1997) Convergent peptide synthesis; in Methods in Enzymol. Ed G. Fields, Academic Press, New York, N.Y. pp 313-335. In this method, linear protected fragments are assembled as fully side chain protected fragments. These fragments can then be coupled together in a convergent manner to assemble the primary sequence of ShK or one of its analogs. Assembly of the fragments could also utilize a solid-phase resin to facilitate coupling and wash steps.

Alternatively, recombinant methods may be used wherein the cDNA coding sequence for ShK could be generated for expression in either a prokaryotic or eucaryotic expression system. Recombinant ShK analogs containing unnatural amino acids are also possible by utilizing preload tRNA molecules which utilize non-standard condons. The cCNA construct can be engineered to use one of these unused codons to add the phosphotyrosine residue as well as the Aeea residue. Folding of the recombinantly produced ShK analog could then be accomplished in a similar method to that used for the synthetic peptides. (See, Pennington, M. W., Byrnes, M. E., Zaydenberg, I., Khaytin, I., de Chastonay, J., Krafte, D., Hill, R., Mahnir, V., Volberg, W. A., Gorczyca, W. and Kem, W. R. (1995) *Int. J. Peptide Protein Res.* 46, 354-358.)

Attaching Anionic Amino Acid Residues to ShK and Optional Modifications to ShK

Anionic amino acid residues may be attached to the N terminus of natural or synthetic ShK Toxin by way of a linker, such as an aminoethyloxyethyloxy-acetyl linker, or bay any other suitable means. In this example, the nine (9) ShK analogs shown in FIG. 1 are prepared. Initially, Fmoc-Aeea-OH is coupled to the N-terminus of synthetic ShK Toxin assembled as described above. The resin is then divided into 9 aliquots. Either Fmoc-Tyr($PO_4$Bzl)-OH, Fmoc-d-Tyr ($PO_4$Bzl)-OH, Fmoc-Tyr($PO_4Me_2$)-OH, Fmoc-Pmp-OH, Fmoc-d-Pmp-OH, Fmoc-Pmp(Et)-OH, Fmoc-Pmp$(Et)_2$—OH, Fmoc-Tyr(tBu)-OH, or Fmoc-Amp(Boc)-OH is then coupled using DIC and HOBT to one of the resin aliquots. The deblocked peptide resin is then cleaved and deprotected with reagent K (King et al., 1990) containing 5% triisopropylsilane for 2 h at RT. Met(O) is reduced by addition of solid $NH_4I$ to the cleavage cocktail at t-15 min. (Nicolas et al., 1995). For the peptide containing Tyr($PO_4Me_2$)-OH, a cleavage cocktail containing 1 M TMSBr in TFA containing thioanisole as a scavenger for 18 hr at 4° C. was used (Tian et al., 1993). Incomplete removal of the methyl protecting groups is common when using this method and two of the species (Tyr($PO_4$) and Tyr($PO_4$Me)) are easily purified by RP-HPLC. The Tyr($PO_4Me_2$) containing analog is cleaved via standard Reagent K cleavage keeping both Me groups intact. In each case, the cleavage mixture is filtered and the crude peptide is precipitated into ice-cold diethyl ether. The precipitate is collected, yielding approximately 75 mg of peptide from 200 mg of resin. The crude product is dissolved in 20 ml of 50% aqueous AcOH and diluted into 0.75 l of $H_2O$. The pH of the solution is adjusted with $NH_4OH$ to 8.2, and it was allowed to fold overnight with the addition of glutathione (2 mM:1 mM) (reduced:oxidized). All analogs are purified using RP-HPLC as described previously (Pennington et al., 1995; Pennington et al., 1996a; Pennington et al., 1996b). Pure fractions are pooled and lyophilized. Each sample is confirmed by RP-HPLC, AAA and MALDI-TOF MS and adjusted to account for peptide content prior to bioassay.

In some embodiments of the invention, to improve the PK/PD properties of the ShK structure, residues which are sensitive to degradation properties may be replaced or substituted. Thus, substitution of the Met residue at position 21 may be carried out to impart a stabilizing effect to oxidation. Additionally, substitution of the C-terminal acid function with an amide will impart stability to C-terminal carboxypeptidase enzymes. These two substitutions to the primary structure of ShK combined with the anionic moiety at the N-terminus have been synthesized to generate the most stable and selective Kv1.3 blocker. Nonhydrolyzable phosphate substitutions will also impart a stabilizing effect versus acid and basic hydrolysis of the phosphate as well as stability against phosphatase enzymes. The substitutions are summarized below. The acronyms used are defined as follows: Pmp=p-phosphonomethyl-Phenylalanine; Ppa=p-Phosphatityl-Phenylalanine and Nle=Norleucine.

Substitutions:

p-phospho-Tyr-Aeea-ShK-Nle21-Cys35-amide
p-Phosphono-methyl-Phenylalanine-Aeea-ShK-Nle21-Cys35amide (Pmp)
p-Phosphatityl-Phe-Aeea-ShK-Nle21-Cys35-amide (Ppa)
p-phospho-Tyr-Aeea-ShK-Nle21-Cys35-acid
p-Phosphono-methyl-Phenylalanine-Aeea-ShK-Nle21-Cys35acid (Pmp)
p-Phosphatityl-Phe-Aeea-ShK-Nle21-Cys35-acid (Ppa)

In addition to the nonhydrolyzable Pmp and Ppa, substitution of p-Phosphono(difluoro-methyl)-Phenylalanine (Pfp) and p-Phosphono-methylketo-Phenylalanine (Pkp) are also anionic substitutions, providing the following:

Pfp-Aeea-Shk-Nle21 Cys35 amide
Pkp-Aeea-ShK-Nle21-Cys35 amide
Pfp-Aeea-Shk-Nle21 Cys35 acid
Pkp-Aeea-ShK-Nle21-Cys35 acid.

Structures of the N-terminal substitutions are set forth in Appendix B. Other structures that are within the scope of the present invention are published in Beeton, C. et al., *Targeting Effector Memory T Cells with a Selective Peptide Inhibitor of Kv1.3 Channels for Therapy of Autoimmune Diseases*, Molecular Pharmacology, Vol. 67, No. 4, 1369-(2005), the entirety of which is expressly incorporated herein by reference and a complete copy of which is appended hereto as Appendix C.

Therapeutic Uses of ShK Analogs of the Present Invention

The present invention provides methods for treating or preventing certain disorders or diseases, such as T cell mediated disorders (e.g., autoimmune disorders, graft vs. host disease, prevention of rejection of organ transplants etc.), other inflammatory disorders, obesity and Type 2 diabetes, in human or animal subjects by administering to the subject a therapeutically effective (e.g., preventative or effective to reduce or eliminate symptoms or disease progression) amount of a pharmaceutically acceptable preparation consisting or comprising an ShK analog of the present invention (e.g., including but not limited to those listed in Table 1 hereabove). Any suitable route of administration (e.g., oral, rectal, intravenous, intramuscular, subcutaneous, intradermal, intranasal, topical, transmucosal, transdermal, by drug delivery implant, etc.) may be used. When used to prevent or treat a T cell mediated disorder, the dosage(s) will be sufficient to inhibit Kv1.3 channels on T cell membranes. In this regard, the ShK analogs of the present invention have the potential to be used to prevent or treat a wide variety of a T cell mediated autoimmune disorders. The following are some examples of some T cell mediated autoimmune diseases that may be prevented or treated by the methods of the present invention, categorized with respect to the target organ that is principally affected by each such disease:

---

Nervous System:

Multiple sclerosis
Myasthenia gravis
Autoimmune neuropathies
such as Guillain-Barré
Autoimmune uveitis
Blood:

---

Autoimmune hemolytic anemia
Pernicious anemia
Autoimmune
Thrombocytopenia
Vascular:

---

Temporal arteritis
Anti-phospholipid syndrome
Vasculitides such as
Wegener's granulomatosis
Behcet's disease
Skin:

---

Psoriasis
Dermatitis herpetiformis
Pemphigus vulgaris
Vitiligo
Gastrointestinal Tract:

---

Crohn's Disease
Ulcerative colitis
Primary biliary cirrhosis
Autoimmune hepatitis
Bone resorption associated
with periodontal disease
Endocrine:

---

Type 1 diabetes mellitus
Addison's Disease
Grave's Disease
Hashimoto's thyroiditis
Autoimmune oophoritis and
orchitis
Multiple Organs and/or
Musculoskeletal System:

---

Rheumatoid arthritis (RA)
Osteoarthritis (OA)
Systemic lupus erythematosus
Scleroderma
Polymyositis, dermatomyositis
Spondyloarthropathies such as
ankylosing spondylitis
Sjogren's syndrome

---

Irrespective of the particular organ(s) affected, T-lymphocytes are believed to contribute to the development of autoimmune diseases. The currently available therapies for these diseases are largely unsatisfactory and typically involve the use of glucocorticoids (e.g. methylprednisolone, prednisone), non-steroidal anti-inflammatory agents, gold salts, methotrexate, antimalarials, and other immunosuppressants such as cyclosporin and FK-506. Also, another T cell mediated disorder that may be prevented or treated by the methods of the present invention is graft vs. host disease and/or rejection of transplanted organs. Indeed, the outcomes of organ transplant procedures have progressively improved with the development of refinements in tissue typing, surgical techniques, and more effective immunosuppressive treatments. However, rejection of transplanted organs remains a major problem. T-lymphocytes play a central role in the immune response and they are responsible, in large measure, for the rejection of many transplanted organs. They are also responsible for the so-called graft-versus host disease in which transplanted bone marrow cells recognize and destroy MHC-mismatched host tissues. Accordingly, drugs such as cyclosporin and FK506 that suppress T-cell immunity are used to prevent transplant rejection and graft-versus-host disease. Unfortunately, these T cell inhibiting drugs are toxic, with liver and renal toxicities limiting their use. Thus, the methods of the present invention may provide les toxic alternatives for the treatment or prevention of graft vs. host disease or transplant rejection. Also, inhibitors of the voltage gated Kv1.3 potassium channel have been shown to be especially effective in suppressing effector memory T cells and, thus, the methods of present invention may be particularly effective in preventing or treating diseases that are associated with effector memory T cells, such as; bone resorption and periodontal disease, psoriasis, rheumatoid arthritis, diabetes mellitus and multiple sclerosis. In addition to T cell mediated diseases, the Kv1.3 channel has been determined to regulate energy homeostasis, body weight and peripheral insulin sensitivity. Thus, the methods of the present invention may be used to treat other diseases and disorders that involve abnormal homeostasis, body weight and peripheral insulin sensitivity by inhibiting Kv1.3 channels on cell membranes, such other diseases and disorders include but are not necessarily limited to bone resorption in periodontal disease, Type 2 diabetes, metabolic syndrome and obesity.

Use of ShK Analogs of the Present Invention in Flow Cytometry

Further in accordance with the present invention there are provided methods for diagnosing T cell mediated disorders or otherwise sorting or distinguishing between various cell types in vitro using fluorophore tagged versions of ShK(L5) for use in flow cytometry alone, or in conjunction with class II tetramers that can detect autoreactive cells. Flow Cytometry is a flexible method for characterizing cells in suspension wherein fluorescence activated cell sorting is used to select living cells on the basis of characteristics measured by flow cytometry. The types of cellular features and functions that may be detected by flow cytometry include the expression of proteins outside and within cells, type of DNA content, viability and apoptosis, multiple drug resistance pump activity, enzyme activity, T-cell activation, T-cell receptor specificity, cytokine expression, phagocytosis and oxidative burst activity. Thus, in this method of the present invention, the amino acid residue attached to the ShK may incorporate a fluorophore tag for use in flow cytometry alone, or in conjunction with class II tetramers loaded with specific autoantigens that can detect autoreactive cells. Specific descriptions of the methods by which such flow cytometry may be carried out are described in Beeton, C., et al., *A Novel Fluorescent Toxin to Detect and Investigate Kv1.3 Channel Up-Regulation in Chronically Activated T Lymphocytes*; J. Biol. Chem., Vol. 278, No. 11, 9928-9937 (March 2003). In general, a flow cytometer uses focused laser light to illuminate cells as they pass the laser beam in a fluid stream. Light scattered by the cells and light emitted by fluorescent dyes attached to cells of interest are analyzed by several detectors and processed by a computer. Cells may be distinguished and selected on the basis of size and shape as well as by the presence of many different molecules inside and on the surface of the cells.
Examples of Potassium Channel Inhibiting Effects and Therapeutic Utility of ShK Analogs of the Present Invention ShK blocks the neuronal Kv1.1 channel and the Kv1.3 channel with roughly equivalent potency. Neurotoxicity is therefore a concern under circumstances that compromise the blood-brain-barrier and allow the entry of sufficient amounts of ShK to block Kv1.1 channels. Our strategy to design a Kv1.3-specific inhibitor was guided by our finding that ShK-F6CA containing fluorescein-6-carboxylate (F6CA) attached through a 20 Å-long Aeea linker to the N-terminus of ShK exhibited 80-fold selectivity for Kv1.3 over Kv1.1 (Beeton et al., 2003). Since F6CA can exist as a restricted carboxylate or also as a cyclized lactone, it was not clear whether ShK-F6CA's Kv1.3 specificity was due to the negative charge of F6CA, the hydrophobicity created by this large bulky fluorescein nucleus, potential planar –p electronic stacking or a combination of all of these potential contributions. To distinguish between these possibilities and with the intention of developing a non-fluorescent Kv1.3-selective inhibitor, we generated a series of 12 novel N-terminally-substituted ShK analogs to probe some of these interactions. By attaching tyrosine, phenylalanine or their derivatives (varying in charge, size and hydrophobicity) through an Aeea linker to the N-terminus of ShK, we could probe the effects of charge and hydrophobicity to gain insight into our selectivity enhancement seen with F6CA substitution.

Selective KV\v1.3 Inhibition over Kv1.1 Inhibition:

In the example shown in FIGS. 2A-2D, L-phosphotyrosine (L-pTyr) a negatively charged (net charge 2) post-translationally modified aromatic amino acid, was attached via the AEEA linker to ShK-$Arg^1$ to generate the novel analog ShK (L5). The ShK toxin and ShK(L5) were tested on Kv1.3 and Kv1.1 channels stably expressed in L929 cells. FIG. 2B shows the effects of ShK and ShK(L5) on Kv1.3 and Kv1.1 currents elicited by 200 ms depolarizing pulses from a holding potential of 80 mV to 40 mV. Both peptides reversibly blocked Kv1.3 and Kv1.1 in a dose-dependent manner with Hill coefficients of 1. $K_d$s were determined from the dose-response curves shown using Microcal Origin software. ShK blocked Kv1.3 ($K_d$=10±1 pM) and Kv1.1 ($K_d$=28±6 pM) with roughly equivalent potency as expected (FIG. 1C). In contrast, ShK(L5) was 100-fold selective for Kv1.3 ($K_d$=69±5 pM) over Kv1.1 ($K_d$=7.4±0.8 nM) (FIGS. 1B, 1C). The time course of Kv1.3 current block by ShK(L5) and its washout is shown in FIG. 1D. The time constant ($T_{ON}$) of ShK(L5) wash-in was 131±21 sec (n=7) while the time constant ($T_{OFF}$) for peptide wash-out was 150±28 sec (n=4). The $K_d$ (57±7 pM) calculated from the KON ($15\times10^6+0.5\times10^6$ $M^{-1}sec^{-1}$) and $K_{OFF}$ (0.0059±0.0013 $sec^{-1}$) values is consistent with the $K_d$ (69±5 pM) determined with Microcal Origin software.

Other ShK analogs were also tested on Kv1.3 and Kv1.1 channels. ShK(D5) containing D-phosphotyrosine (D-pTyr) was 35-fold selective for Kv1.3 over Kv1.1 but was an order of magnitude less potent than ShK(L5). ShK(L6) containing L-pTyr-monomethyl showed modest (11-fold) Kv1.3 specificity, while ShK analogs containing L-pTyr-dimethyl or L-Tyr were not selective for Kv1.3 over Kv1.1. Analogs that contained phenylalanine or its derivatives (varying in bulk, p electron density and charge) were modestly specific or not specific for Kv1.3 over Kv1.1. ShK(L5)'s 100-fold specificity for Kv1.3 over Kv1.1 is greater than that of ShK-F6CA (80-fold), ShK(D5) (35-fold), ShK-$Dap^{22}$ (33-fold) or any other ShK analog tested.

Applicants also assessed ShK(L5)'s specificity on a panel of 20 ion channels and these data are summarized in the following Table 2:

| Channels | $K_d$ of ShK(L5) [pM] |
|---|---|
| Kv1.1 | 7,000 ± 1,000 |
| Kv1.2 | 48,000 ± 7,000 |
| Kv1.3 (cloned) | 69 ± 5 |
| Kv1.3 (native) | 76 ± 8 |
| Kv1.4 | 137,000 ± 3,000 |
| Kv1.5 | 100,000 no effect |
| Kv1.6 | 18,000 ± 3,000 |
| Kv1.7 | 100,000 no effect |
| Kv2.1 | 100,000 no effect |
| Kv3.1 | 100,000 no effect |
| Kv3.2 | 20,000 ± 2,000 |
| Kir2.1 | 100,000 no effect |
| Kv11.1 (HERG) | 100,000 no effect |
| $K_{Ca}1.1$ | 100,000 no effect |
| $K_{Ca}2.1$ | 100,000 no effect |
| $K_{Ca}2.3$ | 100,000 no effect |
| $K_{Ca}3.1$ | 115,000 ± 5,000 |
| Nav1.2 | 100,000 no effect |
| Nav1.4 | 100,000 no effect |
| Swelling-activated T cell $Cl^-$ channel | 100,000 no effect |
| Cav1.2 | 100,000 no effect |

As may be appreciated from the data of Table 2 above, ShK (L5) blocked the Kv1.3 channel in T cells with a $K_d$ (76 pM) equivalent to its $K_d$ on the cloned channel (69 pM). It was 100-fold selective for Kv1.3 over Kv1.1, 260-fold selective over Kv1.6, 280-fold selective over Kv3.2, 680-fold selective over Kv1.2 and >1000-fold selective over all other channels tested. Importantly, it was 1600-fold Kv1.3-selective over KCa3.1, the calcium-activated $K^+$ channel that regulates activation of human naïve and $T_{CM}$ cells (Wulff et al., 2003). Native ShK was less selective than ShK(L5). ShK was 2.8-fold selective for Kv1.3 ($K_d$=10±1 pM) over Kv1.1 ($K_d$ 28±6 pM), 20-fold selective over Kv1.6 (200±20 pM), 500-fold selective over Kv3.2 ($K_d$=5,000±1,000 pM), and >1000-fold selective-over Kv1.2 (10±1 nM) and KCa3.1 ($K_d$=28±3 nM). Margatoxin, a peptide from scorpion venom that has been touted as a specific Kv1.3 inhibitor (Koo et al., 1997; Lin et al., 1993; Middleton et al., 2003) was also not specific. It was 5-fold selective for Kv1.3 (110±12 pM) over Kv1.2 ($K_d$=520±1 pM), 9-fold selective over Kv1.1 (10±1 nM) and >1000-fold selective over Kv1.6 and Kv3.2 ($K_d$>100 nM). Luteolin, a nutriceutical sold for autoimmune diseases (www.lutimax.com) on the basis of it being a Kv1.3 inhibitor (Lahey and Rajadhyaksha, 2004), blocked Kv1.3 weakly ($K_d$=65±5 mM) and exhibited no selectivity over Kv1.1 ($K_d$=77±5 mM), Kv1.2 ($K_d$=63±4 mM) or Kv1.5 ($K_d$=41±3 mM). ShK(L5)'s exquisite specificity for Kv1.3 together with its picomolar affinity for the channel makes it a potentially attractive immunosuppressant.

Preferential Suppression of Human $T_{EM}$ Cell Proliferation

With reference to FIGS. 3A-3D, in order to assess ShK(L5)'s in vitro immunosuppressive activity, Applicants compared its ability to suppress anti-CD3 antibody-stimulated proliferation of human $T_{EM}$ cell lines versus human PBMCs that contain a mixture of naïve and $T_{CM}$ cells. Flow cytometry confirmed the cell surface phenotypes of the two populations studied. As seen in FIG. 3A, the $T_{EM}$ lines were >90% $CCR7^-$CD45RA, while as shown in FIG. 3B the PBMCs contained 65% CCR7$^+$CD45RA$^+$ (naïve) and 18% CCR7$^+$CD45RA$^-$ (T$_{CM}$) cells. FIG. 3C shows that ShK(L5) and ShK were 60-fold more effective in suppressing the proliferation of T$_{EM}$ cells (IC$_{50}$=~80 pM) compared with PBMCs (IC$_{50}$=5 nM, p<0.05). The lower sensitivity of PBMCs might be explained by a rapid up-regulation of KCa3.1 channels in naïve and T$_{CM}$ cells upon stimulation as has been reported previously (Ghanshani et al., 2000; Wulff et al., 2003). In keeping with this interpretation, PBMCs activated for 48 hours to up-regulate KCa3.1 expression, then rested for 12 hours, and re-activated with anti-CD3 antibody were completely resistant to ShK(L5) block, as shown in the upper row of FIG. 3D. PBMCs that had been suppressed by ShK(L5) during the first round of stimulation exhibited identical resistance to ShK(L5) when the cells were washed, rested and re-challenged with anti-CD3 antibody. These results corroborate earlier studies indicating that naïve and T$_{CM}$ cells escape Kv1.3 inhibitors by up-regulating KCa3.1 channels. Thus, ShK(L5) preferentially and persistently suppresses the proliferation of T$_{EM}$ cells.

Preferential Suppression of Rat T$_{EM}$ Cells Proliferation

Figure 4A:
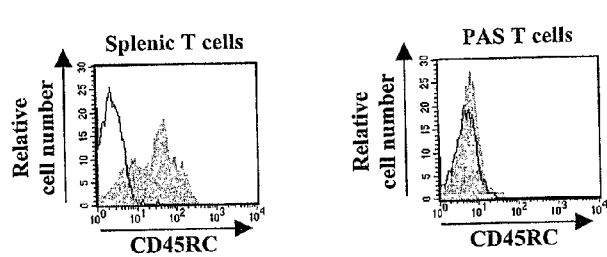
FIG. 4A is a graph showing CD45RC staining of rat splenic T cells (left) and PAS T cells (right) detected by flow cytometry.
Figure 4B:
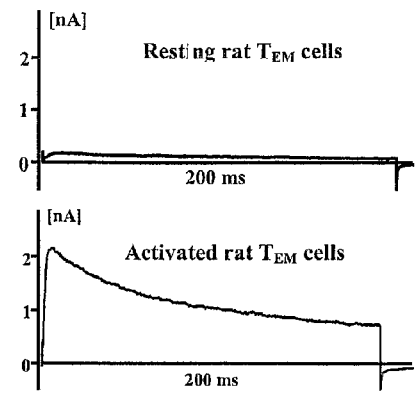
FIG. 4B is a graphic showing of Kv1.3 currents exhibited by quiescent (top) and myelin antigen-activated (bottom) PAS T cells.
Figure 4C:
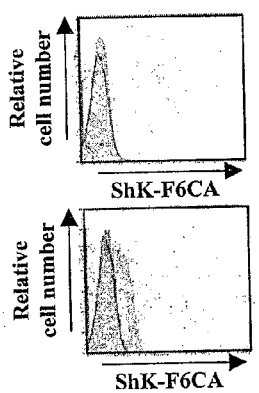
FIG. 4C provides a graphic representation of flow cytometry profiles of ShK-F6CA-staining in quiescent (top) and myelin antigen-activated (bottom) PAS T cells. Unstained cells (black lines) and cells stained with ShK-F6CA (area filled in light grey). Competition of ShK-F6CA staining by unlabeled ShK(L5) is represented by the area filled in dark grey.
Figure 4D:
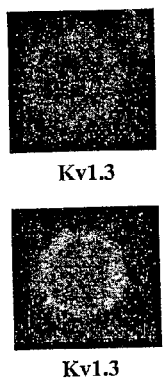
FIG. 4D shows confocal images of Kv1.3 immunostaining in quiescent (top) and myelin antigen-activated (bottom) PAS T cells. Statistical analysis was carried out using the Mann-Whitney U-test.

As a preamble to evaluating ShK(L5)'s therapeutic effectiveness we examined its ability to suppress proliferation of a memory T cell line, PAS, that causes an MS-like disease in rats. As a control, Applicants used rat splenic T cells. To confirm the differentiation status of the two cell populations we assessed the expression of CD45RC, a marker of naïve T cells (Bunce and Bell, 1997). Rat splenic T cells were 76% CD45RC$^+$ (i.e. mainly naïve cells) whereas PAS cells were CD45RC$^-$ suggesting that they are memory cells, as shown in FIG. 4A. To determine whether PAS cells are in the T$_{EM}$ or the T$_{CM}$ state we examined Kv1.3 expression before and 48 hours after activation. T$_{EM}$ but not T$_{CM}$ cells are expected to significantly up-regulate Kv1.3 levels upon stimulation. With reference to FIG. 4B, patch-clamp experiments revealed a striking increase in Kv1.3 current amplitude after MBP-stimulation of PAS cells consistent with their being T$_{EM}$ cells. As an independent measure of the number of Kv1.3 channels on PAS cells, we used ShK-F6CA, a fluorescently labeled ShK analog that has previously been reported to bind specifically to Kv1.3. The intensity of ShK-F6CA staining determined by flow cytometry reflects the number of Kv1.3 tetramers expressed on the cell surface. As seen in FIG. 4C, ShK-F6CA (10 nM) staining intensity increased with MBP-activation of PAS cells and an excess of unlabeled ShK(L5) (100 nM) competitively inhibited ShK-F6CA staining. As a final test, Applicants performed confocal microscopy on quiescent and MBP-stimulated PAS cells that had been fixed and stained with a Kv1.3-specific antibody. In keeping with data in FIGS. 4B and 4C, resting PAS T cells had a Kv1.3 staining intensity of 4.4±0.6 and this value increased to 10.6±2.3 (p<0.005) after antigen-induced activation (See FIG. 4D) showing augmentation in Kv1.3 protein expression following activation. Thus, MBP-activated PAS cells are CD45RC$^-$ Kv1.3$^{high}$ T$_{EM}$ cells whereas rat splenic T cells used in our experiments are predominantly in the naïve state.

Figure 4E:
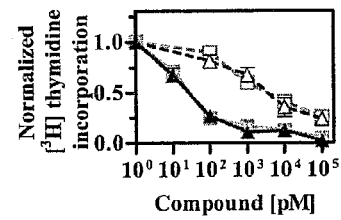
FIG. 4E shows dose-dependent inhibition by ShK (dark lines) and ShK(L5) (light lines) of [$^3$H] thymidine incorporation by rat (left) naïve/$T_{CM}$ (open symbols) and $T_{EM}$ (closed symbols) cells activated with Con A (1 μg/ml).
Figure 4F:
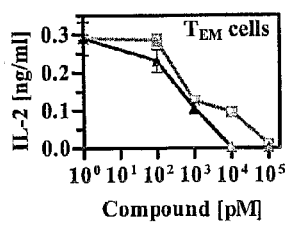
FIG. 4F shows dose-dependent inhibition by ShK (dark lines) and ShK(L5) (light lines) of IL2 secretion by PAS T cells 7 hours after stimulation with MBP.
Figure 4G:
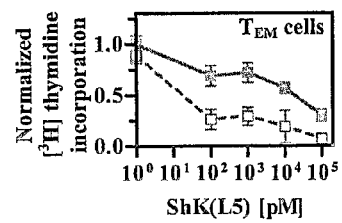
FIG. 4G, ShK(L5)-induced inhibition of myelin-antigen triggered [$^3$H] thymidine incorporation by PAS T cells (open symbols) is reversed by the addition of 20 u/ml IL2 (closed symbols).

MBP-triggered proliferation of PAS cells was suppressed ~1000-fold more effectively by ShK(L5) and ShK (IC$_{50}$=~80 μM) than mitogen-induced proliferation of rat splenic T cells (See FIG. 4E, IC$_{50}$ ~100 nM; p<0.05). These results corroborate the findings with human T cells described above. As seen in FIG. 4G ShK(L5) inhibited MBP-induced IL2 production by PAS cells (FIG. 4F), and exogenous IL2 partially over-rode ShK(L5) suppression of PAS cell proliferation (FIG. 4G). Earlier studies reported similar findings with less specific Kv1.3 inhibitors on human, rat and mini-pig T cells. In summary, ShK(L5) is a powerful and selective inhibitor of human and rat T$_{EM}$ cells, and may therefore have therapeutic use in autoimmune diseases by preferentially targeting T$_{EM}$ cells that contribute to the pathogenesis of these disorders.

Circulating Half-Life and Stability

A patch-clamp bioassay was used to ascertain whether circulating levels of ShK(L5) following subcutaneous injection were sufficient to inhibit T$_{EM}$ cells. The results of these experiments are shown in FIGS. 5A-5F.

Serum samples from ShK(L5)-treated and control rats were tested for blocking activity on Kv1.3 channels. Control serum did not exhibit detectable blocking activity indicating an absence of endogenous channel blockers. To standardize the assay, known amounts of ShK(L5) were added to rat serum and these samples were tested on Kv1.3 channels. The spiked serum samples blocked Kv1.3 currents in a dose-dependent fashion (K$_d$ 77±9 μM) that was indistinguishable from ShK(L5)'s effect in the absence of serum (FIG. 4A). Levels of ShK(L5) in treated animals were determined by comparison with the standard curve. ShK(L5) was detectable in serum 5 minutes after a single subcutaneous injection of 200 mg/kg. Peak levels (12 nM) were reached in 30 minutes and the level then fell to a baseline of about 300 pM over 420 minutes. The disappearance of ShK(L5) from the blood could be fitted by a single exponential. The circulating half-life was estimated to be ~50 min.

Since the peak serum level after 200 mg/kg (12 nM) significantly exceeds the requirement for selective blockade of Kv1.3 channels and T$_{EM}$ cell function, we tested lower doses. After a single injection of 10 mg/kg the peak serum concentration of ShK(L5) reached ~500 pM within 30 min (data not shown), a concentration sufficient to block >90% Kv1.3 but not affect Kv1.1. Repeated daily administration of this dose (10 mg/kg/day) resulted in steady-state levels of ~300 pM (measured 24 hours after injection, FIG. 5D), which is sufficient to cause 60-70% suppression of T$_{EM}$ cells with little effect on naïve/T$_{CM}$ cells. The "steady-state" level is unexpected given the estimated circulating half-life of ~50 min and indicates that ShK(L5) "accumulates" on repeated administration. To determine whether the "depot" was in the skin or elsewhere in the body, we measured blood levels of ShK(L5) 10 hours after rats received single intravenous or subcutaneous injections of 10 mg/kg ShK(L5). The peptide disappeared with the same time course following administration by either route (FIG. 5E) indicating that the skin is not responsible for the steady-state level of 300 pM ShK(L5) reached after a single 10 mg/kg daily injection (FIG. 5D), and the depot(s) resides elsewhere.

The successful achievement of a steady-state level of 300 pM ShK(L5) following daily single injections of 10 mg/kg/day suggests that the peptide may be stable in vivo. To directly examine its stability we incubated ShK(L5) in rat plasma or in PBS containing 2% rat plasma at 37° C. for varying durations and then measured Kv1.3 blocking activity. In both sets of spiked samples (plasma and PBS) we observed a 50% reduction in Kv1.3-blocking activity in about 5 hours, presumably due to peptide binding to the plastic surface of the tube, and the level then remained steady for the next 2-days (FIG. 5F). As an added test of stability we compared the Kv1.3- versus Kv1.1-blocking activities of sera from ShK(L5)-treated rats. If ShK(L5) is modified in vivo, either by dephosphorylation of pTyr or cleavage of the Aeea-pTyr side-chain, it would yield ShK(L4) and ShK respectively, neither of which is selective for Kv1.3 over Kv1.1. Serum samples from ShK (L5)-treated animals exhibited the same selectivity for Kv1.3 over Kv1.1 as ShK(L5), indicating that the peptide does not undergo the modifications stated above. Taken together, these results indicate that ShK(L5) is remarkably stable in plasma and attains pharmacologically relevant serum concentrations after single daily subcutaneous injections of 10 mg/kg.

Nontoxicity

Applicants conducted several in vitro and in vivo tests to determine if ShK(L5) exhibits any toxicity. The results of these studies are summarized in Appendix A. Human and rat lymphoid cells incubated for 48 hours with a concentration (100 nM) of ShK(L5)>1200 times greater than the Kv1.3 half-blocking dose or the $IC_{50}$ for $T_{EM}$ suppression (70-80 pM), exhibited minimal cytotoxicity. The same high concentration of ShK(L5) was negative in the Ames test on tester strain TA97A suggesting that it is not a mutagen. Both in vitro tests failed to detect any significant toxicity.

Drug-induced blockade of Kv11.1 (HERG) channels has contributed to major cardiac toxicity and the withdrawal of several medications from the market. ShK(L5) has no effect on Kv11.1 channels at 100 nM (>1430-fold the $K_d$ for Kv1.3), and Applicants' chosen therapeutic regimen (10 mg/kg/day, 300 pM steady-state circulating level) should therefore not cause cardiotoxicity.

As a further test, Applicants performed heart rate variability analysis in conscious rats administered vehicle (PBS+2% rat serum) on day-1, followed by 10 mg/kg/day ShK(L5) on day-2. ShK(L5) had no effect on heart rate or the standard HRV (heart rate variability) parameters in both time and frequency domains (Task force of the European Society of Cardiology and the North American Society of Pacing Electrophysiology, 1996).

Encouraged by the acute toxicity experiments, Applicants performed a sub-chronic toxicity study in which rats were administered daily subcutaneous injections of 10 mg/kg ShK(L5) or vehicle for 2 weeks (n=6 in each group).

ShK(L5)-treated animals gained weight to the same degree as rats receiving vehicle (Appendix A). Hematological and blood chemistry analysis showed no difference between ShK(L5)- and vehicle-treated rats, and flow cytometric analysis revealed no differences in the proportions of thymocyte or lymphocyte subsets (Appendix A). Collectively, these studies suggest that ShK(L5) is safe.

To determine the therapeutic safety index, we administered a 60-fold higher dose (600 mg/kg/day) of ShK(L5) to healthy rats for 5 days and observed no clinical signs of toxicity, and no toxicity was seen when healthy rats received a single injection of 1000 mg/kg ShK(L5). The situation is less sanguine when the blood-brain-barrier is compromised as happens in EAE and MS. Rats with EAE that received ShK(L5) 10 mg/kg/day for 10 days showed no signs of toxicity. In contrast, forty percent of rats (5/12) administered 600 mg/kg/day for five days died on the fifth day when they developed clinical signs of EAE (extrapolated $LD_{50}$=750 mg/kg/day). Since the peak concentration of ShK(L5) in the serum (12 nM) after administration of a single injection of 200 mg/kg is sufficient to block >50% of Kv1.1 channels, toxicity observed in EAE rats administered 600 mg/kg/day ShK(L5) is likely due to the ingress into the brain of sufficient amounts of ShK(L5) to block Kv1.1. Thus, the effective therapeutic safety index of ShK(L5) is well in excess of 100 in situations where the blood-brain barrier is not compromised (as seen in autoimmune diseases that do NOT affect the central nervous system (CNS)), whereas the therapeutic safety index is 75 when the blood-brain barrier is breached.

Prevention of DTH and Acute Adoptive EAE

Figure 6A:
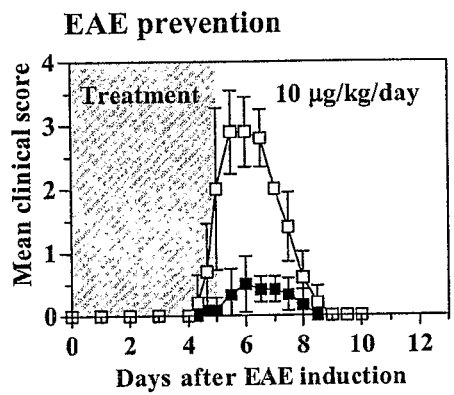
FIG. 6A is a graph showing scored prevention of EAE. PAS T cells were activated in vitro, washed, and injected intraperitoneally on day 0. Clinical scoring of EAE: 0=no clinical signs, 0.5=distal limps tail, 1=limp tail, 2=mild paraparesis or ataxia, 3=moderate paraparesis, 4=complete hind limb paralysis, 5=4+incontinence, 6=death. Rats (n=6/group) were injected subcutaneous with vehicle alone (n=6) or ShK (L5) (n=6; 10 mg/kg/day) from day 0 to day 5.
Figure 6B:
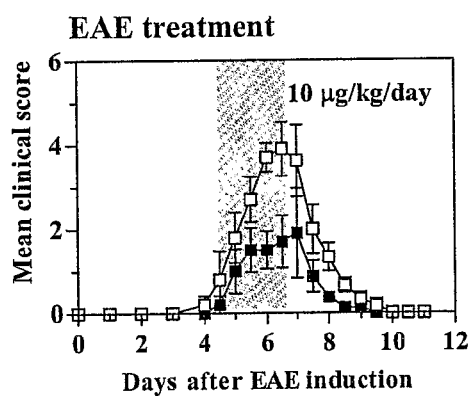
FIG. 6B is a graph showing scored treatment of EAE. PAS T cells were activated in vitro, washed, and injected intraperitoneally on day 0. Treatment with ShK(L5) at 10 mg/kg/day was started when rats developed clinical signs of EAE and was continued for 3 days.
Figure 6C:
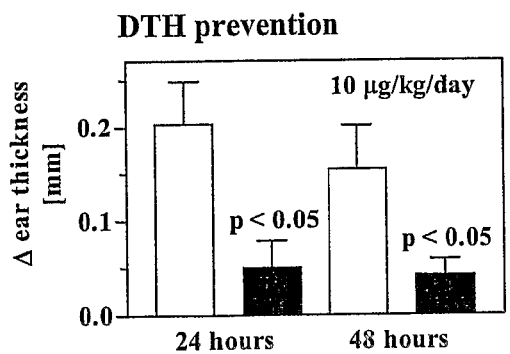
FIG. 6C is a graph showing ear thickness as an indicator of DTH reaction elicited against ovalbumin in rats. Animals (n=6/group) were treated with ShK(L5) 10 mg/kg/day for 2 days, after which ear swelling was measured. Statistical analysis was carried out using the Mann-Whitney U-test.

With reference to FIGS. 6A-6C, ShK(L5) was evaluated for immunosuppressive activity in vivo in two animal models. Applicants tested its ability to prevent and treat acute EAE induced by the transfer of MBP-activated PAS $T_{EM}$ cells into Lewis rats, as well as to suppress the DTH reaction mediated by $T_{EM}$ cells. PAS cells were activated with MBP for 48 hours in vitro and then adoptively transferred (6-8×10$^6$ viable cells) into Lewis rats. For the prevention trial, rats then received subcutaneous injections of saline (controls) or ShK(L5) (10 µg/kg/day) for 5 days. In the first prevention trial control rats developed mild EAE (mean maximum clinical score 2.0±1.2) with an average onset of 5.6±0.6 days (not shown). ShK(L5) reduced disease severity (mean maximum clinical score 0.7±0.6, p<0.05). In the second prevention trial, control rats developed more severe EAE (mean maximum clinical score 3.2±0.4) with a mean onset of 4.8±0.4 days (FIG. 6A). ShK (L5) significantly reduced disease severity (mean maximum clinical score 0.6±0.4, p<0.007) but did not significantly delay disease onset (5.5±0.7 days; p=0.07). No signs of toxicity were noted in these studies.

In the treatment trial (FIG. 6B) rats were injected with MBP-activated PAS cells, administered saline or 10 µg/kg/day ShK(L5) when they initially developed signs of EAE (limp tail, hunched posture and loss of 6% or more of their weight over 24 hours) and therapy was continued for three days. Clinical signs of EAE peaked on day 6 in the control group (score=3.9±0.7) and on day 7 in the treated group (score=1.9±0.9; p<0.05).

As an independent assessment of ShK(L5)'s immunosuppressive activity in vivo, Applicants also examined its effectiveness in inhibiting the DTH reaction that is mediated predominantly by skin-homing $T_{EM}$ cells. Lewis rats immunized with ovalbumin and adjuvant were challenged 7 days later with ovalbumin in one ear and saline in the other ear. Rats then received injections of saline (controls) or ShK(L5) (10 µg/kg/day) and ear thickness was measured as an indication of DTH. All control rats developed ear swelling 24 and 48 hours after ovalbumin challenge while the DTH reaction was substantially milder in ShK(L5)-treated animals (FIG. 6C). Thus, ShK(L5) inhibits the $T_{EM}$-mediated DTH response, and prevents and ameliorates severe adoptive EAE induced by myelin-activated $T_{EM}$ cells.

Figure 7A:
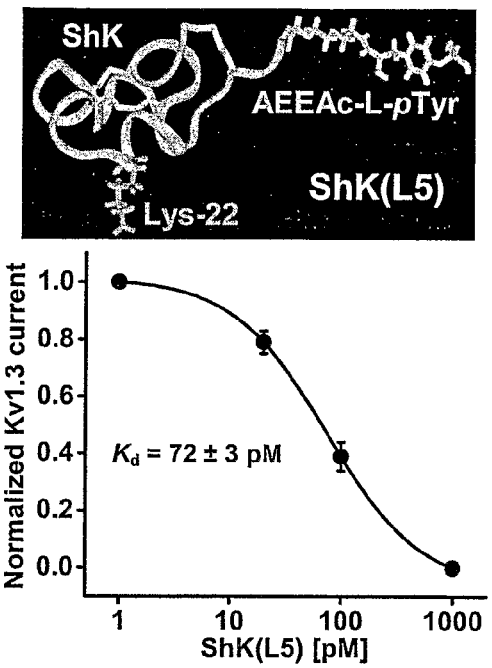
FIG. 7A shows the ShK(L5) structure and a graph showing inhibition of Kv1.3 channels in $T_{EM}$ cells as a function of ShK(L5) concentration. Each data-point represents mean of three determinations.
Figure 7B:
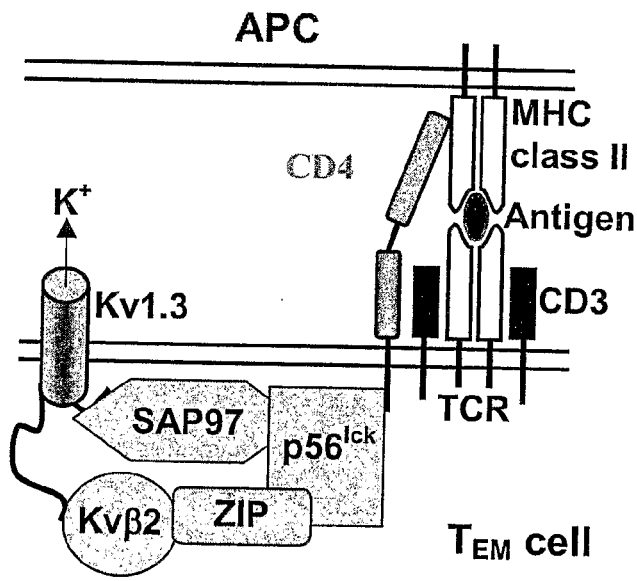
FIG. 7B is a diagram of Kv1.3-containing signaling complex.
Figure 7C:
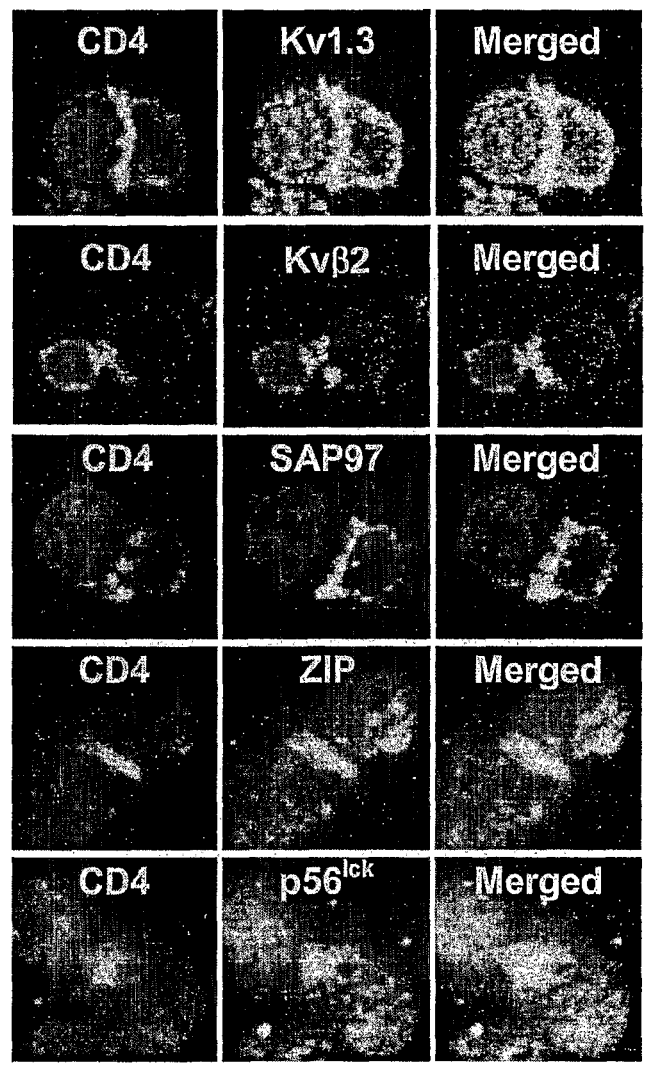
FIG. 7C shows co-localization of CD4, Kv1.3, Kvβ2, SAP97, ZIP and p56$^{lck}$ at IS.
Figure 7D:
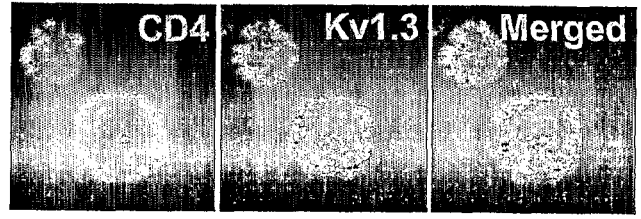
FIG. 7D shows CD4 and Kv1.3 staining in absence of visible $T_{EM}$-APC contact.
Figure 7E:
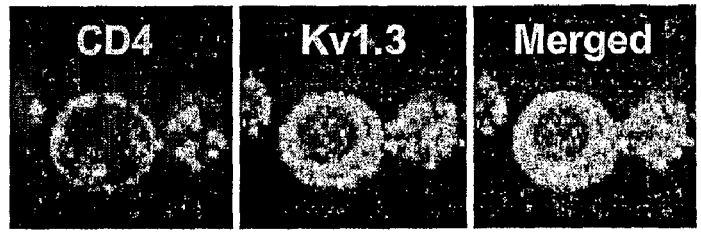
FIG. 7E shows CD4 and Kv1.3 staining in GAD65-specific $T_{EM}$ cells exposed to MBP-loaded APCs.
Figure 7F:
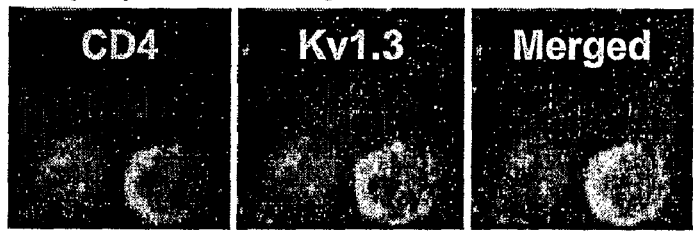
FIG. 7F shows that ShK(L5) 100 nM does not prevent IS formation.
Figure 7G:
FIG. 7G shows that ShK(L5) 100 nM does not disrupt the IS.

Kv1.3 Clusters at the IS During Antigen Presentation but K$^+$ Efflux Through Kv1.3 is Not Required for IS Formation or Stability Referring to FIGS. 7A-7G, ShK(L5), a highly selective Kv1.3 inhibitor (21), blocked Kv1.3 currents in GAD65-specific $T_{EM}$ cells with a $K_d$ of 72±3 pM. We used ShK(L5) as a pharmacological probe to define those steps in $T_{EM}$ cell activation that require Kv1.3 function. Biochemical studies have shown that Kv1.3 and Kvb2 belong to a signaling complex that includes SAP97 (Synapse-Associated-Protein-97), ZIP (PKC-zeta-interacting-protein, p56$^{lck}$-associated-p62-protein, A170), $p_{56}^{lck}$ and CD4 (FIG. 7B). The existence of this complex in human $T_{EM}$ cells is supported by Applicants' results showing co-capping of Kv1.3, Kvb2, SAP97, ZIP and $p_{56}^{lck}$ with CD4. Furthermore, FRET (fluorescence energy transfer) studies show Kv1.3 in close proximity to CD3 in Kv1.3-transfected human T cells, and the channel preferentially localizes at the point of contact between Kv1.3-transfected human cytotoxic T cells and their targets. Since CD4 traffics to the IS, the zone of contact between T cells and antigen presenting cells (APC), it is possible that Kv1.3 and other proteins in the signaling complex also localize at the IS during antigen-presentation. To test this idea, GAD65-specific Kv1.3$^{high}$ $T_{EM}$ clones from a T1DM patient were incubated with HLA-matched APCs that had been loaded with GAD65 5571 peptide and stained with DAPI to aid visualization. After 20 min, APC-$T_{EM}$ conjugates were immunostained for proteins in the signaling complex. CD4 co-localized at the IS with Kv1.3, Kvb2, SAP97, ZIP and $p_{56}^{lck}$. In the absence of APC-$T_{EM}$ contact, CD4 and Kv1.3 were distributed throughout the cell. Furthermore, CD4 and Kv1.3 failed to localize at points of contact when GAD65-specific $T_{EM}$ cells were exposed to APCs loaded with MBP (an irrelevant antigen), verifying that IS-clustering is antigen-specific. Thus in GAD65-specific $T_{EM}$ cells, a Kv1.3-containing signaling complex traffics together with CD4 to the IS during antigen-presentation, suggesting that Kv1.3 is an integral component of the machinery that transduces signals in $T_{EM}$ cells. Based on these studies, ShK(L5) at a concentration that blocks approximately 99% of Kv1.3 channels (100 nM) did not prevent IS-clustering and did not disrupt the IS once formed, indicating that $K^+$ efflux through Kv1.3 channels is unnecessary for IS formation or stability.

Suppression of Human $T_{EM}$ Cells

Figure 8A:
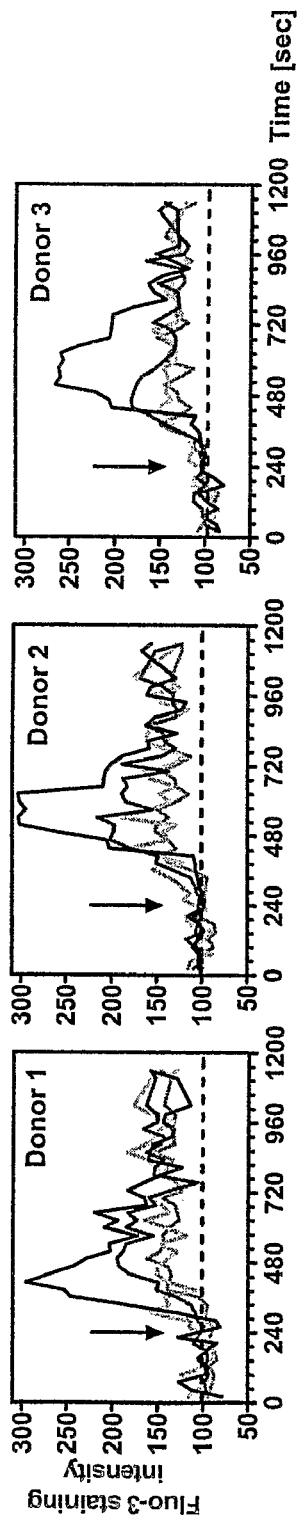
FIG. 8A is a graphic showing of calcium signaling in GAD-specific $T_{EM}$ cells from three T1DM patients triggered by anti-CD3+cross-linking secondary antibodies (arrow) in the absence (black) or presence of ShK(L5) 0.1 nM (dark grey), 1 nM (medium grey) or 100 nM (light grey).
Figure 8B:
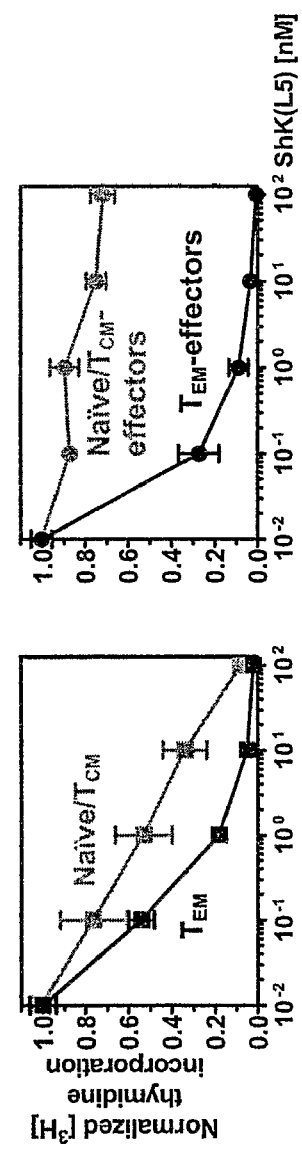
FIG. 8B is a graph showing [$^3$H]-thymidine incorporation by naïve/$T_{CM}$ and $T_{EM}$ cells (left) and naïve/$T_{CM}$-effectors and $T_{EM}$-effectors from patients with T1DM and RA (right). $T_{EM}$ cells: GAD65-activated $T_{EM}$ clones from three T1DM patients and anti-CD3 antibody activated SF-$T_{EM}$ cells from three RA patients. Naïve/$T_{CM}$ cells: anti-CD3 antibody-activated PB-naïve/$T_{CM}$ cells from the same three RA patients.
Figure 8C:
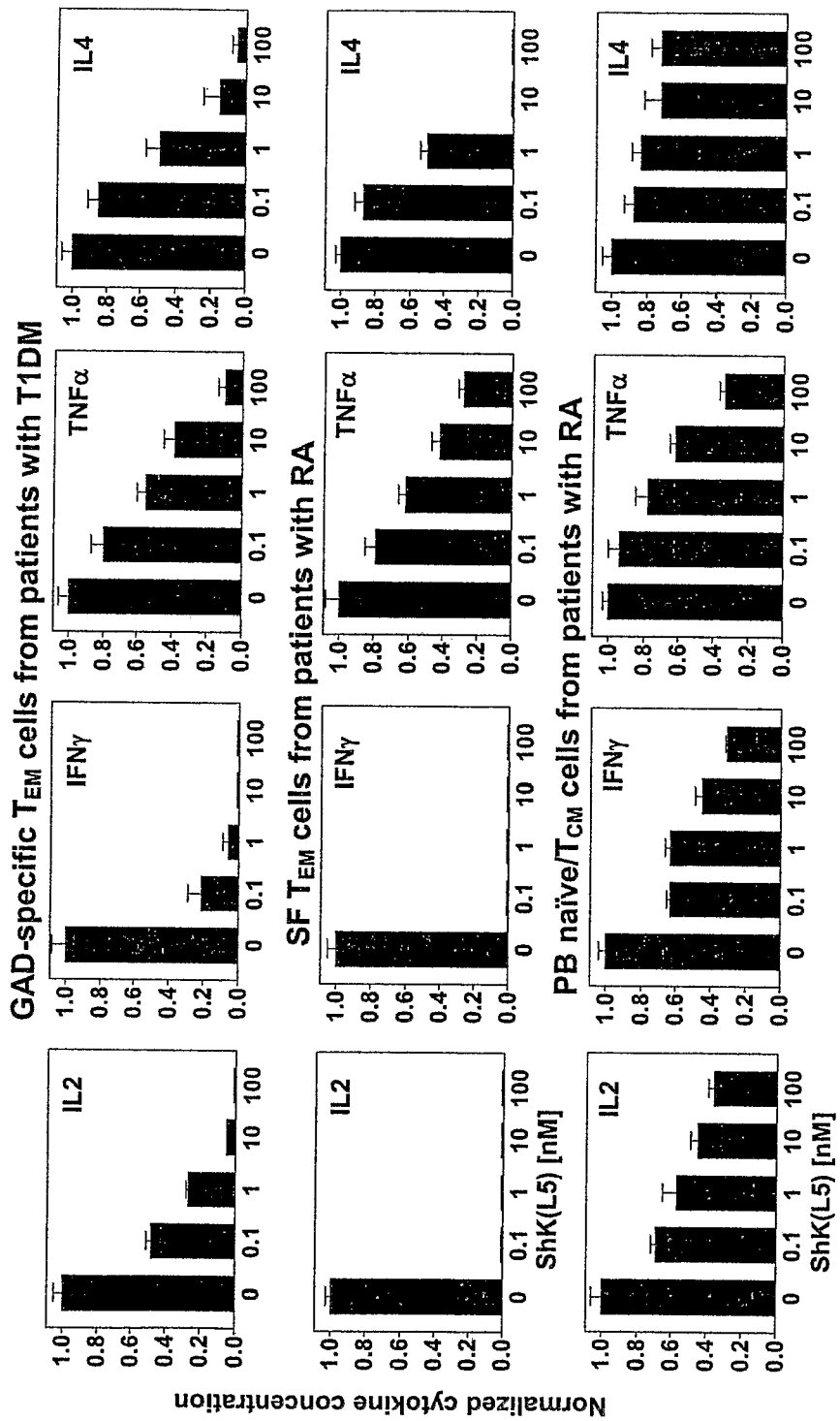
FIG. 8C is a series of bar graphs showing Cytokine production by the $T_{EM}$ and naïve/$T_{CM}$ cells used in FIG. 8B.
Figure 8D:
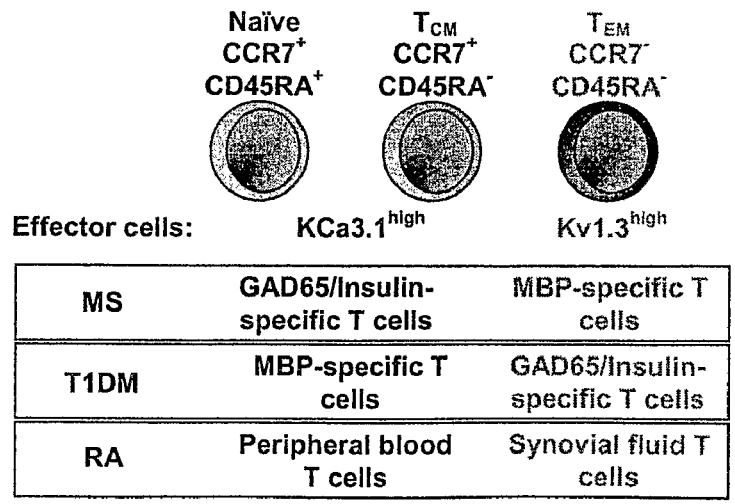
FIG. 8D shows the phenotype of disease-relevant and disease-irrelevant autoreactive T cells in MS, T1DM and RA.
Figure 8E:
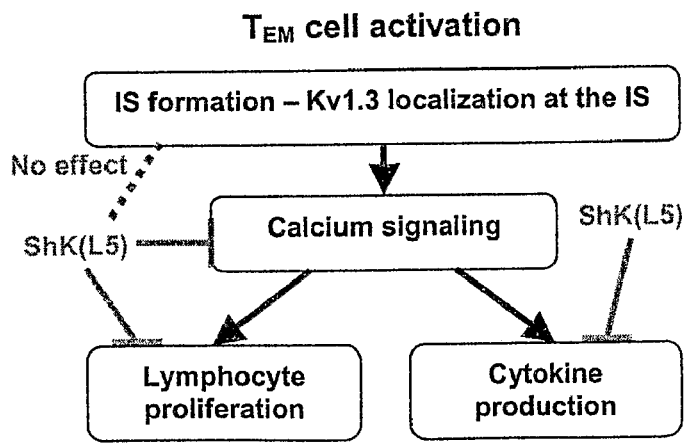
FIG. 8E is a diagram showing the manner in which ShK (L5) inhibits calcium signaling, lymphocyte proliferation and cytokine production but not IS formation.

With reference to FIGS. 8A-8E, ShK(L5) inhibited calcium signaling in $T_{EM}$ cells, an early and essential step in T cell activation. GAD65-specific $T_{EM}$ clones from T1DM patients were loaded with the calcium indicator dye Fluo3, pre-incubated in medium alone or with increasing concentrations of ShK(L5) and imaged by flow cytometry before and after the addition of an activating anti-CD3 antibody and a cross-linking secondary antibody. Peak calcium rise occurred in 242±35 seconds after stimulation and was blocked by ShK(L5) with an $IC_{50}$ of ~200 pM (FIG. 8A). ShK(L5) was 10-fold more effective in suppressing [$^3$H]-thymidine-incorporation by autoreactive $T_{EM}$ cells from T1DM and RA patients compared with naïve/$T_{CM}$ cells from these patients (FIG. 8B, left). In a second set of experiments (FIG. 8B, right), RA-SF and RA-PB T cells were activated with anti-CD3 antibody for 48 hours to generate "$T_{EM}$-effectors" and "naïve/$T_{CM}$-effectors" respectively. Cells were rested overnight in medium, re-stimulated with anti-CD3 antibody in the presence or absence of ShK(L5) for a further 48 hours and [$^3$H]-thymidine incorporation was measured. RA-SF-$T_{EM}$-effectors retained their sensitivity to ShK(L5) inhibition, whereas RA-PB-naïve/$T_{CM}$-effectors were resistant to Kv1.3 blockade (FIG. 8B, right), most likely because they up-regulate the calcium-activated KCa3.1/IKCa1 channel, which substitutes for Kv1.3 in promoting calcium entry. ShK(L5) profoundly suppressed the production of interleukin 2 (IL2) and interferon-g (IFN-g) by $T_{EM}$ cells from T1DM and RA patients, whereas IL2 and IFN-g production by naïve/$T_{CM}$ cells from these patients was less affected (FIG. 8C). The production of tumor necrosis factor-a and interleukin 4 by both $T_{EM}$ cells and naïve/$T_{CM}$ cells was less sensitive to ShK (L5) (FIG. 8C).

Verification of Rat Model of Delayed Type Hypersensitivity (DTH) Caused by Effector Memory T Cells.

As shown in FIG. 9, rats were immunized with ovalbumin (OVA) in adjuvant. They were challenged in one ear 7 days later with OVA and in the other ear with saline. Ear swelling was measured 24 h later as a sign of delayed type hypersensitivity (DTH). The FACS histograms shown in FIG. 9 indicate that T cells in the ears challenged with OVA are CD45RC-negative memory cells while T cells in the blood and spleen of the same rats are mostly naïve T cells.

Figure 10:
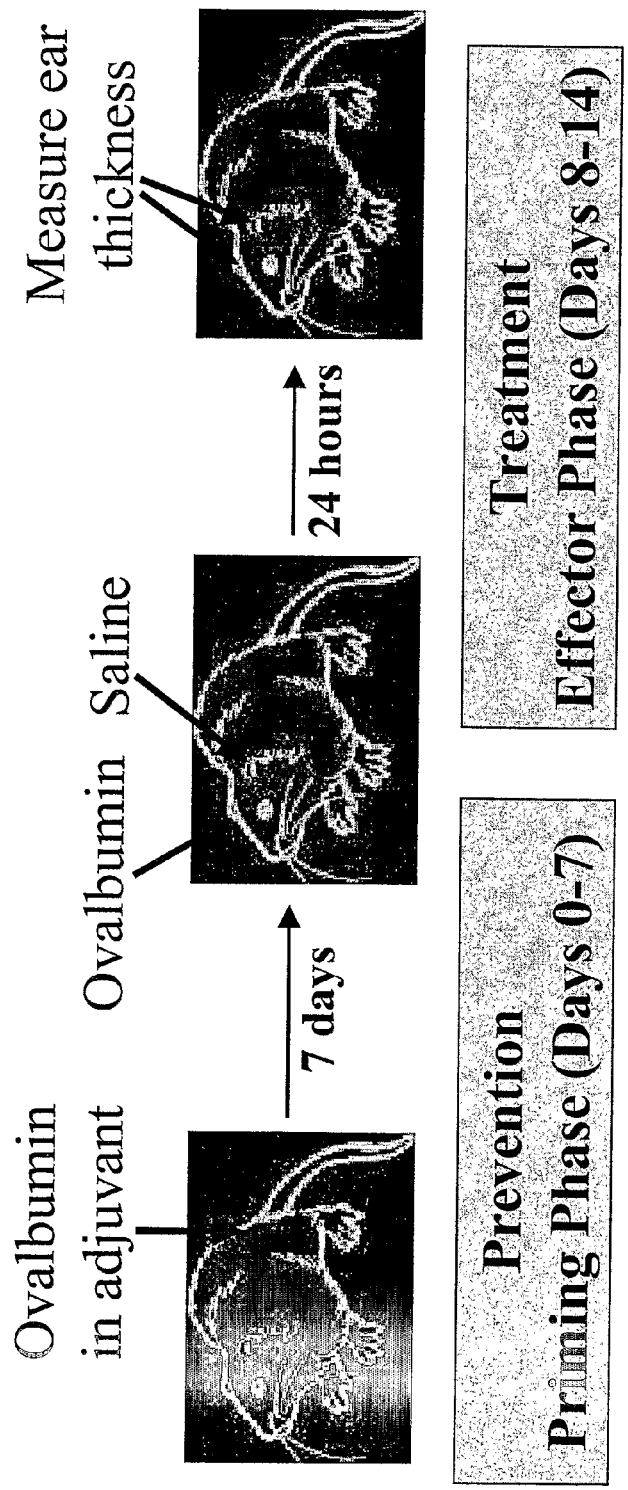
FIG. 10 is a diagram showing a treatment protocol for ShK(L5) in a rat model of delayed type hypersensitivity (DTH) caused by effector memory T cells

Treatment Protocol for Shk(L5) in a Rat Model of Delayed Type Hypersensitivity (DTH) Caused by Effector Memory T Cells As shown in FIG. 10, rats received ShK(L5) 10 μg/kg/day as a subcutaneous injection either from day 0 to day 7 (during the priming phase) to prevent the differentiation of naiv cells to effector memory $T_{EM}$ cells, or during the effector phase after challenge to the ear with ovalbumin to prevent the function of the $T_{EM}$ cells.

Figure 11:
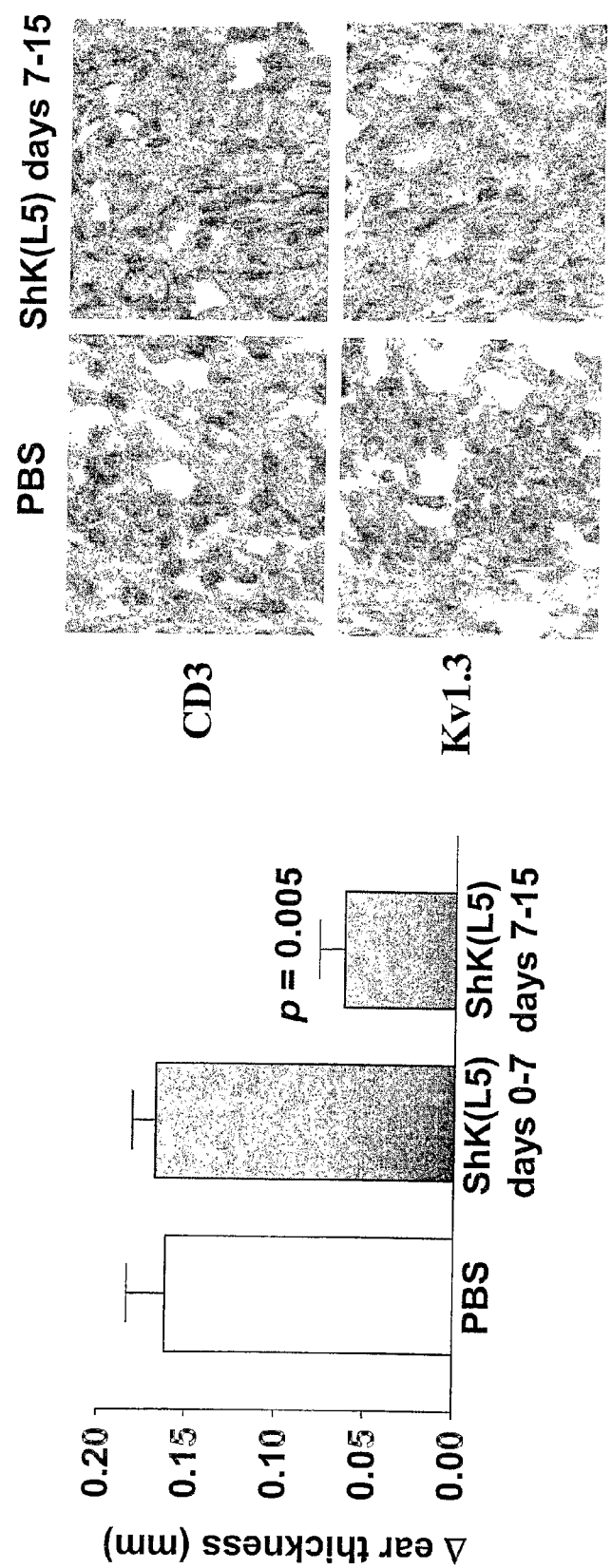
FIG. 11 is a diagram representing specific suppression of effector memory responses in vivo in rats by ShK(L5) without impairing the function of naïve and central memory T cells or B cells.

Shk(L5) Specifically Suppresses Effector Memory Responses In Vivo in Rats Without Impairing the Function of Naïve and Central Memory T Cells or B Cells As shown in FIG. 11, control rats developed ear swelling i.e. a positive DTH response. ShK(L5) was NOT effective in suppressing DTH when administered during the priming phase, indicating that it did not suppress the differentiation of naïve and central memory T cells into effector memory cells. ShK(L5) suppressed DTH when administered during the effector phase indicating that it either prevented the ability of effector memory T cells to reach the ear and/or suppressed the activation of effector memory T cells. The first possibility was excluded because the number of T cells in the ears of ShK (L5)-treated rats was the same as in the ears of rats given the vehicle. ShK(L5) suppressed effector memory T cell activation in the ear because these T cells were Kv1.3-negative, while the memory T cells in the ears of vehicle-treated animals were Kv1.3 positive. IgM and IgG B-cell responses in these animals was also not affected.

Figure 12A:
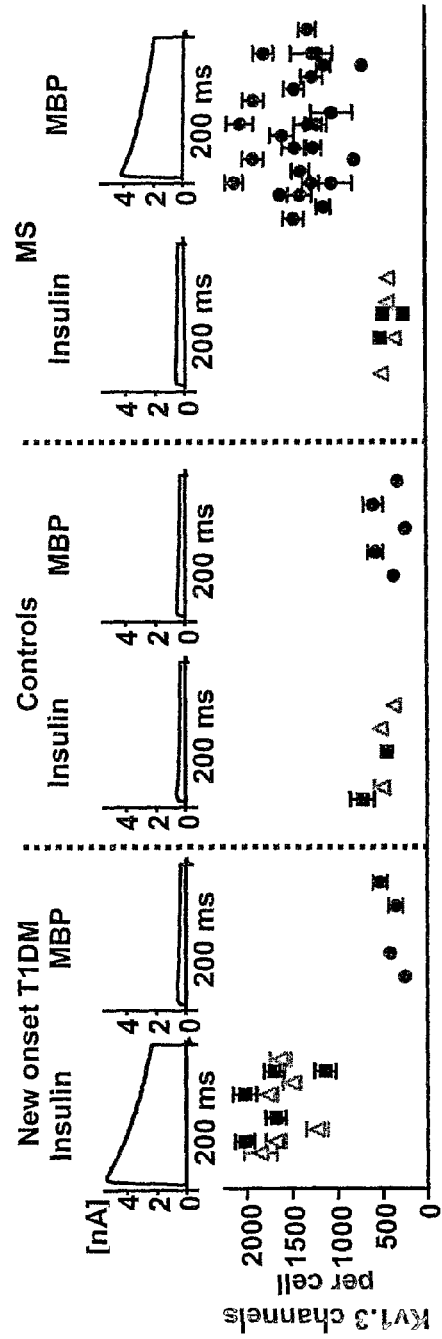
FIG. 12A shows Kv1.3 currents (top) and channel number/cell (bottom) in GAD65-, insulin and myelin-specific T cells from patients with new onset type-1 diabetes mellitus (T1DM), health controls and patients with multiple sclerosis.
Figure 12B:
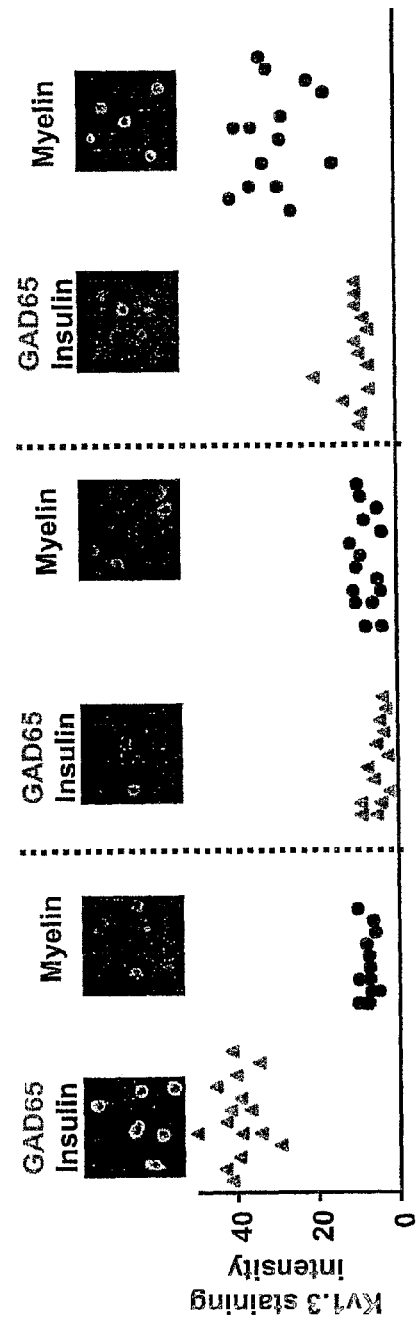
FIG. 12B shows Kv1.3 staining (top) and fluorescence intensities of individual T cells (bottom) from these patients.
Figure 12E:
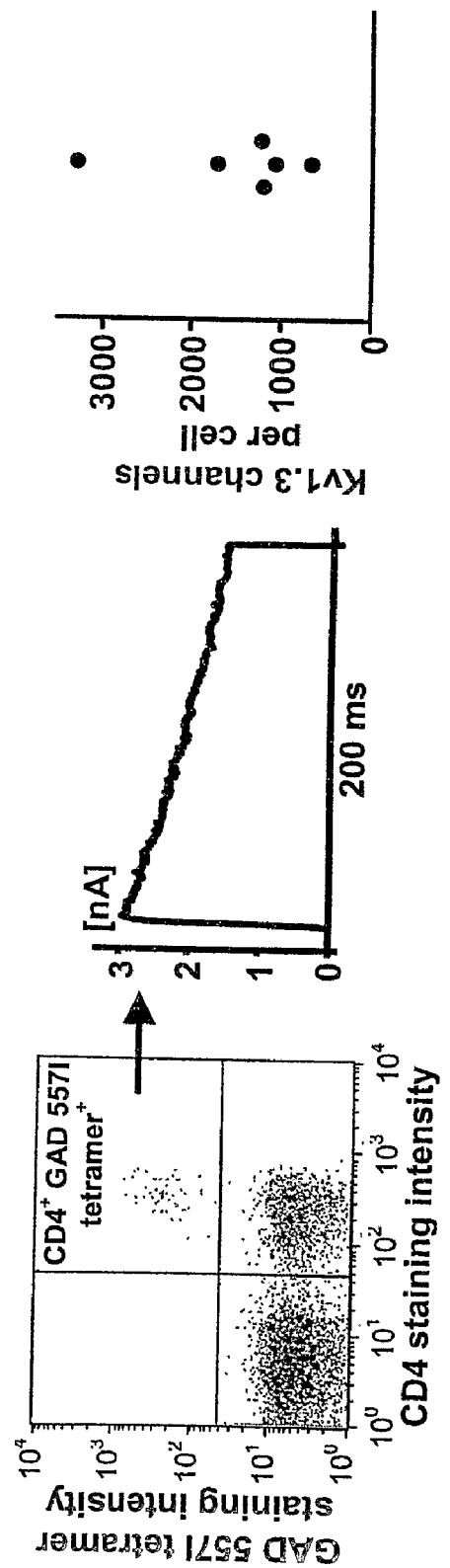
FIG. 12E shows Kv1.3 numbers in CD4$^+$GAD65-tetramer$^+$ T cells from a patient with new-onset T1DM.

Kv1.3 Expression in T Cells Specific for GAD65/555-567, Insulin/9-23- and Myelin Antigens from Patients with T1DM or MS and Healthy Controls FIG. 12A shows Kv1.3 currents (top) and channel number/cell (bottom) from antigen-specific T cells from patients with new onset type-1 diabetes mellitus, health controls and patients with mulitple sclerosis. Each data-point represents the mean ±SEM from 20-50 cells from 24 T cell lines from a single donor measured 48 hours after the third antigen stimulation. Due to the low frequency of T cells specific for insulin and GAD65 in the blood of T1DM patients and controls, we amplified these populations by generating short-term autoantigen-specific CD4$^+$ T cell lines using the split-well method. As controls, we generated T cell lines specific for the irrelevant autoantigen myelin basic protein (MBP) that is implicated in MS but not T1DM. Following the third antigenic stimulation, Kv1.3 currents were measured by whole-cell patch-clamp in activated cells with a membrane capacitance greater than 4 pF (cell diameter ≧11 μm). Representative Kv1.3 currents and Kv1.3 channel-numbers/T cell are shown in FIG. 12A. The currents displayed biophysical and pharmacological properties characteristic of Kv1.3. T cells specific for insulin (9-23) or GAD65 (555-567) from patients with new onset T1DM displayed large Kv1.3 currents and expressed high numbers of Kv1.3 channels, whereas disease-irrelevant MBP-specific T cells from these patients were Kv1.3$^{low}$ (p=0.001). For comparison we have plotted our published Kv1.3 data on MS patients in whom the opposite pattern was observed. In MS patients, T cells specific for MBP or myelin oligodendrocyte glycoprotein (peptide 35-55) or proteolipid protein (peptide 139-151) were Kv1.3$^{high}$, while insulin- and GAD65-specific T cells were Kv1.3$^{low}$ (p=0.0001). Autoreactive T cells isolated from healthy controls were Kv1.3$^{low}$ regardless of specificity. In one individual with both MS and T1DM, T cells specific for all three autoantigens were Kv1.3$^{high}$. GAD65-specific and insulin-specific T cells from patients with longstanding T1DM were Kv1.3$^{high}$ reflecting the persistence of autoreactive $T_{EM}$ cells, whereas a Kv1.3$^{low}$ pattern was found in GAD65- and insulin-specific T cells from patients with non-autoimmune type-2 DM. As seen in FIG. 12B, Kv1.3 staining (top) and fluorescence intensities of individual cells (bottom). Applicants confirmed the patch-clamp data by immunostaining for Kv1.3. Insulin- and GAD65-specific T cells from T1DM patients and MBP-specific T cells from MS patients stained brightly whereas cells specific for irrelevant autoantigens stained dimly. FIG. 12C shows CCR7 expression. Flow cytometry revealed that Kv1.3$^{high}$ T cells were CCR7$^-$ $T_{EM}$ cells, while Kv1.31w cells were CCR7$^+$ naïeve or $T_{CM}$ cells. FIG. 12D shows Kv1.3 number/cell in autoreactive T cells from a patient with both T1DM and MS, and from patients having T1DM or type-2 DM for greater than 5 years and 2 years, respectively. FIG. 12E shows Kv1.3 numbers in CD4$^+$ GAD65-tetramer$^+$ T cells from patient with new-onset T1DM. As a further control, we used fluorescent MHC class II tetramers containing the GAD65 557I peptide, to isolate GAD65-specific CD4$^+$ T cells from a DR-0401-positive patient with new onset T1DM. Tetramer-sorted GAD65-activated T cells displayed the same Kv1.3$^{high}$ pattern observed in GAD65-specific T cell lines from T1DM patients. In summary, disease-relevant, autoantigen-activated T cells in both T1DM and MS are Kv1.3$^{high}$CCR7$^-$ $T_{EM}$-effectors, while disease-irrelevant autoreactive cells in these patients are Kv1.3$^{low}$CCR7$^+$ naïve/$T_{CM}$ cells.

Kv1.3 expression in Rheumatoid Arthritis and Osteoarthritis

Figure 13A:
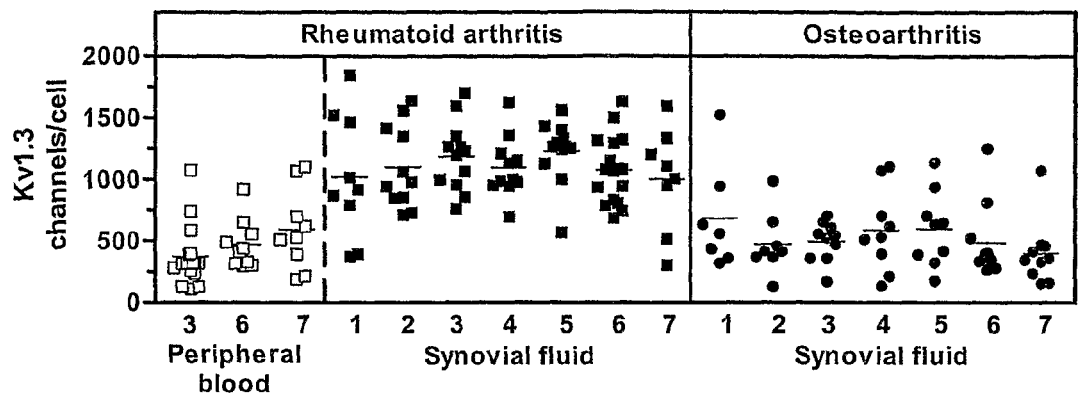
FIG. 13A shows Kv1.3 channel numbers per cell in peripheral T cells blood and synovial fluid T cells of RA patients and synovial fluid T cells of OA patients.
Figure 13B:
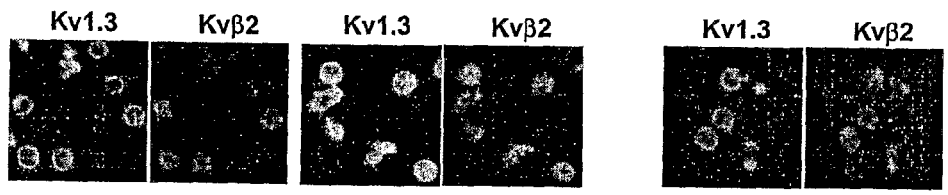
FIG. 13B shows confocal images of Kv1.3 (light grey) and Kvβ2 (darker grey) staining in the cells shown in FIG. 13A.
Figure 13C:
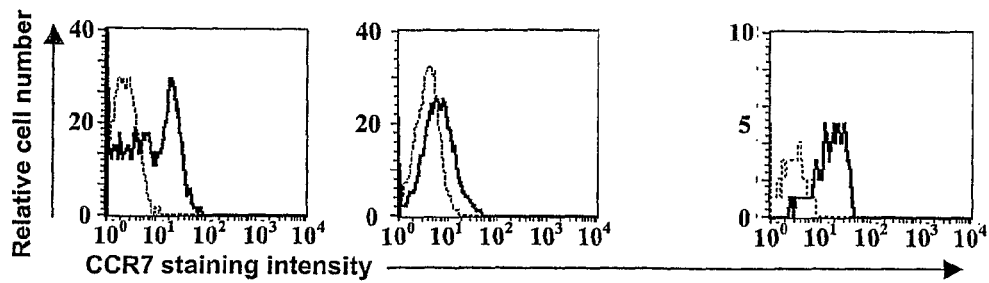
FIG. 13C shows graphs of relative cell number vs. CCR7 staining intensity.
Figure 13D:
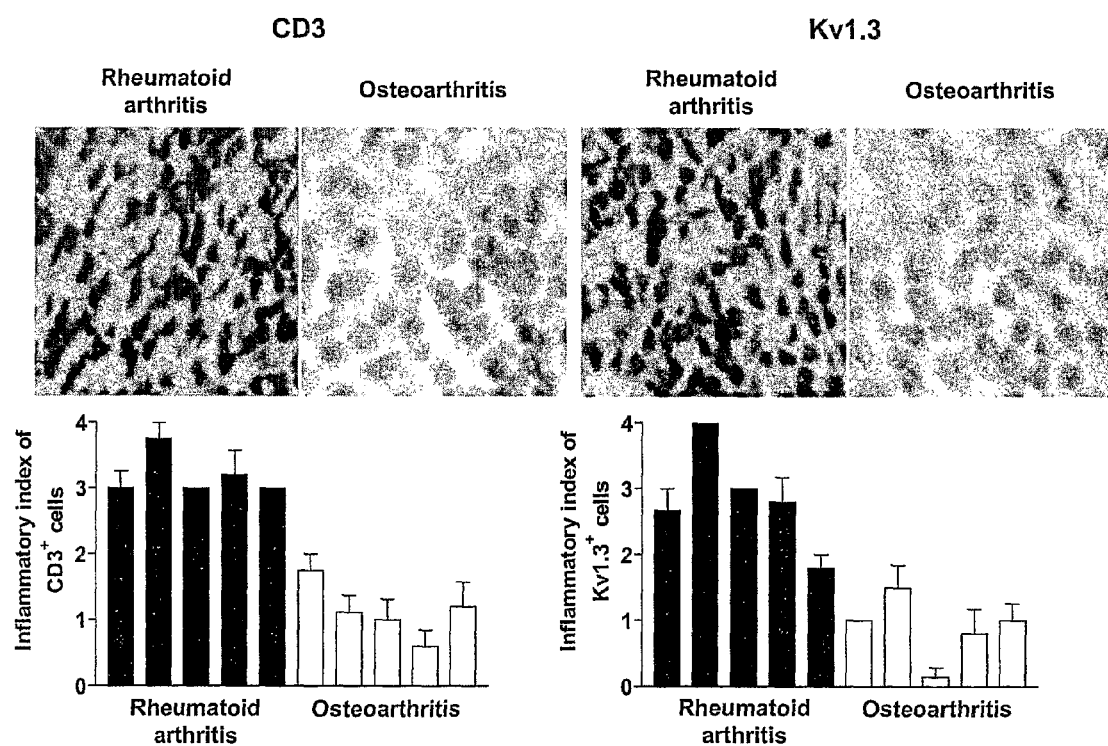
FIG. 13D shows micrographs (top) and bar graphs of inflammatory index (bottom) of synovium from RA and OA patients stained with anti-CD3 or anti-Kv1.3 antibodies and counter-stained with hematoxylin/eosin (40×).

In RA, disease-relevant T cells can be isolated from affected joints. Applicants patch-clamped T cells from the synovial fluid (SF) of 7 RA patients 48 hours after stimulation with anti-CD3 antibody. As seen in FIG. 13A, as controls Applicants analyzed SF-T cells from 7 patients with degenerative, non-autoimmune osteoarthritis (OA) (which had been activated with the same protocol. RA-SF T cells were Kv1.3$^{high}$ whereas OA-SF T cells were Kv1.3$^{low}$ (p<0.0001). Applicants found the Kv1.3$^{low}$ pattern in anti-CD3-activated T cells from the peripheral blood (PB) of RA patients (p<0.0001) because autoreactive Kv1.3$^{high}$ $T_{EM}$ cells are infrequent in the blood. Immunostaining for Kv1.3 and its associated Kvβ2 subunit corroborated the patch-clamp data. FIG. 13B shows confocal images of Kv1.3 (light grey as seen in the figure) and Kvβ2 (darker grey as seen in the figure) staining. RA-SF T cells stained brightly for both Kv1.3 and Kvβ2, while OA-SF and RA-PB T cells displayed weak staining. FIG. 13C illustrates CCR7 expression. Flow cytometry verified that Kv1.3$^{high}$ RA-SF T cells were CCR7$^-$ $T_{EM}$ cells, while Kv1.3$^{low}$ OA-SF and RA-PB T cells were CCR7$^+$ naïve/$T_{CM}$ cells. FIG. 13D (top) shows micrographs of synovium from RA and OA patients stained with anti-CD3 or anti-Kv1.3 antibodies and counter-stained with hematoxylin/eosin (40×). As a further test, we immunostained paraffin-embedded synovial tissues (ST) from 5 RA and 5 OA patients for CD3, Kv1.3 and CCR7. We have previously shown that our staining method does not detect Kv1.3 in naïve/$T_{CM}$ cells because of their low numbers of Kv1.3 channels. In RA-ST, a preponderance of CD3$^{30}$ Kv1.3$^+$CCR7$^-$ $T_{EM}$ cells was seen, whereas CD3$^+$ cells were sparse in OA-synovium and these were mainly Kv1.3$^-$CCR7$^+$ naïve/$T_{CM}$ cells. Degree of infiltration by CD3$^+$, Kv1.3$^+$ and CCR7$^+$ cells assessed by grading system in FIG. S2A. CD3$^+$-inflammatory-index: RA=3.2±0.1; OA=1.1±0.2 (p<0.01); Kv1.3$^+$-inflammatory-index: RA=2.8±0.3; OA=0.6±0.3 (p<0.01). Thus, in three different autoimmune disorders, our results are consistent with disease-associated autoreactive T cells being Kv1.3$^{high}$CCR7$^-$$T_{EM}$-effectors.

It is to be appreciated that the invention has been described herein with reference to certain examples or embodiments of the invention but that various additions, deletions, alterations and modifications may be made to those examples and embodiments without departing from the intended spirit and scope of the invention. For example, any element or attribute of one embodiment or example may be incorporated into or used with another embodiment or example, unless to do so would render the embodiment or example unsuitable for its intended use. Also, where the steps of a method or procedure are listed or stated in a particular order, the order of those steps may be changed unless otherwise specified or unless such change in the order of the steps would render the invention unpatentable or unsuitable for its intended use. All reasonable additions, deletions, modifications and alterations are to be considered equivalents of the described examples and embodiments and are to be included within the scope of the following claims.

APPENDIX A

| Toxicity study of ShK(L5) | |
|---|---|
| In vitro tests | 100 nM ShK(L5) |
| Cytotoxicity (% dead cells) | |
| Human PBMCs | 7.5 ± 4.3 |
| PAS T cells | 8.1 ± 0.8 |
| Jurkat cells | 5.5 ± 3.3 |
| Burkitt lymphoma | 3.1 ± 0.9 |
| RPMI 8226 myeloma | 6.5 ± 2.1 |
| Ames Test | Negative |
| Acute in vivo tests | Saline | ShK(L5) 10 µg/kg |
| Electrocardiogram* | | |
| Heart rate | 302 ± 13 | 311 ± 20 |
| SDNN | 13.3 ± 3.0 | 17.8 ± 4.4 |
| CV % | 6.7 ± 1.4 | 9.2 ± 2.2 |
| SDANN$_{5\,min}$ | 5.0 ± 2.0 | 6.9 ± 2.3 |
| rMSSD | 6.8 ± 2.2 | 9.8 ± 3.5 |
| HF (n.u.) | 71 ± 21 | 79 ± 37 |
| HF (%) | 50 ± 8 | 53 ± 10 |
| LF (n.u.) | 68 ± 4 | 64 ± 10 |
| LF (%) | 50 ± 8 | 47 ± 10 |
| LF/HF | 1.1 ± 0.4 | 1.3 ± 0.7 |
| Sub-chronic in vivo tests | Saline | ShK(L5) 10 µg/kg/day for 2 weeks |
| Weight gain (%) | 7.2 ± 1.8 | 6.2 ± 1.7 |
| Complete blood count | | |
| Hematocrit (%) | 40.3 ± 1.4 | 39.0 ± 4.9 |
| Hemoglobin (g/dl) | 15.3 ± 0.5 | 15.0 ± 1.5 |
| MCV (fl) | 48.5 ± 0.2 | 48.3 ± 0.3 |
| MCH (pg) | 18.5 ± 0.8 | 18.5 ± 0.6 |
| MCHC (g/dl) | 38.0 ± 1.8 | 38.4 ± 1.3 |
| Total white cells (×10$^3$ mm$^{-3}$) | 7.1 ± 2.1 | 7.1 ± 2.5 |
| Total red cells (×10$^6$ mm$^{-3}$) | 8.3 ± 0.3 | 8.1 ± 1.0 |
| Total platelets (×10$^3$ mm$^{-3}$) | 656 ± 214 | 606 ± 106 |
| Blood chemistry | | |
| Alkaline phosphatase (U/l) | 170 ± 26 | 150 ± 18 |
| Glucose (mg/dl) | 139 ± 21 | 150 ± 18 |
| Blood urea nitrogen (mg/dl) | 17.1 ± 2.6 | 15.0 ± 1.7 |
| Creatinine (mg/dl) | 0.6 ± 0 | 0.6 ± 0.1 |
| Albumin (g/dl) | 5.0 ± 0.3 | 4.5 ± 0.4 |
| Thymic cell populations (%) | | |
| CD4$^-$CD8$^-$ | 3.6 ± 1.1 | 4.3 ± 0.7 |
| CD4$^+$CD8$^+$ | 77.8 ± 6.1 | 76.8 ± 4.1 |
| CD4$^+$CD8$^-$ | 8.5 ± 1.7 | 11.2 ± 2.0 |

APPENDIX A-continued

Toxicity study of ShK(L5)

| CD4⁻CD8⁺ | 10.0 ± 3.3 | 7.6 ± 1.3 |
|---|---|---|
| CD3⁺ | 89.5 ± 1.6 | 93.2 ± 3.5 |
| Splenic populations (%) | | |
| CD3⁺ | 72.4 ± 4.4 | 65.4 ± 0.1 |
| CD3⁺CD45RC⁺ | 35.6 ± 2.6 | 39.8 ± 1.1 |
| CD3⁺CD45RC⁻ | 23.6 ± 2.3 | 26.5 ± 1.3 |
| CD3⁺CD4⁺ | 62.7 ± 0.1 | 66.6 ± 1.2 |
| CD3⁺CD8⁺ | 26.9 ± 0.1 | 25.0 ± 0.2 |
| IgM⁺ | 38.8 ± 1.5 | 33.3 ± 0.3 |

Data expressed as mean ± SD.
*Tested with t-tests, $p < 0.05$ on all parameters; SDNN: Standard deviation of all normal-to-normal RR intervals; CV %: 100 × SDNN/average RR interval; $SDANN_{5\ min}$: Standard deviation of the mean of normal RR intervals for each 5 min period; rMSSD: Root mean square of successive difference; HF (n.u.): High frequency (0.75-2.5 Hz) power in normalized unit; LF (n.u.): Low frequency (0.2-0.75 Hz) power in normalized unit.

APPENDIX B

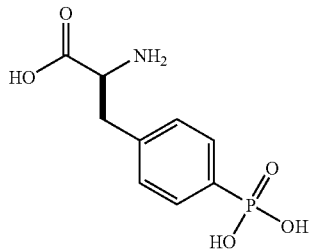

L-p-Phosphonophenylalanine (PPA)

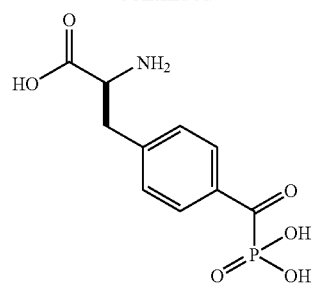

L-p-Phosphonomethanonephenylalanine (PM(=O)PA)
(L-p-Ketophosphonophenylalanine (KPP))

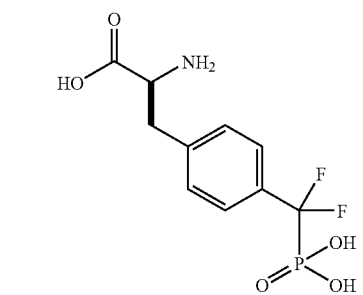

L-p-Phosphonodifluromethyl-phenylalanine (PM(f2)PA)
(L-p-Difluoromethylphosphonophenylalanine)

---

What is claimed is:

1. A composition of matter comprising ShK attached to a chemical entity that has an anionic charge, said chemical entity comprising an entity selected from; AEEAc-L-Tyr $(PO_3H_2)$, AEEAc-L-Pmp$(OH_2)$, AEEAc-D-Pmp$(OH_2)$, AEEAc-D-Pmp(OH, Et), AEEAc-L-Pmp$(Et_2)$, AEEAc-D-Pmp$(Et_2)$, AEEAc-L-Tyr, AEEAc-L-Phe(p-$NH_2$), AEEAc-L-Phe(p-$CO_2$H), AEEAc-L-Aspartate, AEEAc-D-Aspartate, AEEAc-L-Glutamate, or AEEAc-D-Glutamate, wherein said chemical entity is attached to the N-terminal residue of ShK.

2. A composition according to claim 1 wherein the ShK toxin is obtained from a natural source.

3. A composition according to claim 1 wherein the ShK toxin is synthetic.

4. A composition according to claim 1 wherein the chemical entity includes a fluorophore tag.

5. A composition according to claim 1 wherein said chemical entity comprises AEEAc-L-Pmp(OH$_2$).

6. A composition according to claim 1 wherein said chemical entity comprises AEEAc-D-Pmp(OH$_2$).

7. A composition according to claim 1 wherein said chemical entity comprises AEEAc-D-Pmp(OH, Et).

8. A composition according to claim 1 wherein said chemical entity comprises AEEAc-L-Pmp(Et$_2$).

9. A composition according to claim 1 wherein said chemical entity comprises AEEAc-D-Pmp(Et$_2$).

10. A composition according to claim 1 wherein said chemical entity comprises AEEAc-L-Tyr.

11. A composition according to claim 1 wherein the chemical entity comprises AEEAc-L-Phe(p-NH$_2$).

12. A composition according to claim 1 wherein the chemical entity comprises AEEAc-L-Phe(p-CO$_2$H).

13. A composition according to claim 1 wherein the chemical entity comprises AEEAc-L-Aspartate.

14. A composition according to claim 1 wherein the chemical entity comprises AEEAc-D-Aspartate.

15. A composition according to claim 1 wherein the chemical entity comprises AEEAc-L-Glutamate.

16. A composition according to claim 1 wherein the chemical entity comprises AEEAc-D-Glutamate.

17. A composition according to claim 1 wherein said chemical entity comprises AEEAc-L-Tyr(PO$_3$H$_2$).

18. A composition according to claim 1 wherein said ShK has the amino acid sequence: Arg-Ser-Cys-Ile-Asp-Thr-Ile-Pro-Lys-Ser-Arg-Cys-Thr-Ala-Phe-Gln-Cys-Lys-His-Ser-Met-Lys-Tyr-Arg-Leu-Ser-Phe-Cys-Arg-Lys-Thr-Cys-Gly-Thr-Cys (SEQ ID NO:1).

19. A composition of matter having the sequence: p-phospho-Tyr-AEEAc-Arg-Ser-Cys-Ile-Asp-Thr-Ile-Pro-Lys-Ser-Arg-Cys-Thr-Ala-Phe-Gln-Cys-Lys-His-Ser-Met-Lys-Tyr-Arg-Leu-Ser-Phe-Cys-Arg-Lys-Thr-Cys-Gly-Thr-Cys (SEQ ID NO:2).

20. A composition of matter having the sequence: p-phospho-Tyr-AEEAc-Arg-Ser-Cys-Ile-Asp-Thr-Ile-Pro-Lys-Ser-Arg-Cys-Thr-Ala-Phe-Gln-Cys-Lys-His-Ser-Met-Lys-Tyr-Arg-Leu-Ser-Phe-Cys-Arg-Lys-Thr-Cys-Gly-Thr-Cys-amide (SEQ ID NO:3).

21. A composition of matter having the sequence: Tyr-AEEAc-Arg-Ser-Cys-Ile-Asp-Thr-Ile-Pro-Lys-Ser-Arg-Cys-Thr-Ala-Phe-Gln-Cys-Lys-His-Ser-Met-Lys-Tyr-Arg-Leu-Ser-Phe-Cys-Arg-Lys-Thr-Cys-Gly-Thr-Cys-amide (SEQ ID NO:4).

22. A method for causing inhibition of Kv1.3 potassium channels in a human or animal subject, said method comprising the step of:
    (A) administering to the subject a composition according to any of claims 1, 2-3, 4-10, 11-16 and 17-20, in a form and amount that is effective to inhibit Kv1.3 potassium channels.

23. A method according to claim 22 wherein the method is carried out to treat an autoimmune disorder.

24. A method according to claim 23 wherein the autoimmune disorder is selected from the group consisting of:
    Multiple sclerosis;
    Myasthenia gravis;
    Autoimmune neuropathies;
    Guillain-Barre Syndrome;
    Autoimmune uveitis;
    Crohn's Disease;
    Ulcerative colitis;
    Primary biliary cirrhosis;
    Autoimmune hepatitis;
    Autoimmunethrombocytopenia;
    Type 1 diabetes mellitus;
    Addison's Disease;
    Grave's Disease;
    Hashimoto's thyroiditis;
    Autoimmune oophoritis;
    Autoimmune orchitis;
    Behcet's disease;
    Rheumatoid arthritis;
    Bone resorption associated with periodontal disease;
    Systemic lupus erythematosus;
    Scleroderma;
    Polymyositis, dermatomyositis;
    Pemphigus vulgaris;
    Spondyloarthropathies;
    Ankylosing spondylitis; and
    Sjogren's syndrome.

25. A method according to claim 22 wherein the method is carried out to prevent or treat graft vs. host disease.

26. A method according to claim 22 wherein the method is carried out to treat or prevent rejection of a transplanted tissue or organ.

27. A method according to claim 22 wherein the method is carried out to prevent or treat metabolic syndrome.

28. A method according to claim 22 wherein the method is carried out to treat or prevent Type 2 diabetes.

29. A method according to claim 22 wherein the method is carried out to treat or prevent obesity.

30. A method according to claim 22 wherein the method is carried out to treat or prevent bone resorption associated with periodontal disease.

31. A method for performing flow cytometry, said method comprising the steps of:
    (A) providing a composition according to claim 4;
    (B) combining the composition provided in Step A with cells; and
    (C) using a flow cytometer to count, isolate, or distinguish cells that have affinity for the composition provided in Step A.

32. A method according to claim 31 wherein Step C comprises using the flow cytometer to count, isolate or distinguish T lymphocytes.

33. A composition according to claim 1 wherein the ShK is modified by substitution of the Met residue at position 21.

34. A composition according to claim 33 wherein the substitution at Met residue 21 deters oxidation.

35. A composition according to claim 1 wherein the ShK is modified by substitution of the of the C-terminal acid function with an amide.

36. A composition according to claim 35 wherein the substitution of the C-terminal acid function with an amide imparts stability to C-terminal carboxypeptidase enzymes.

37. A method according to claim 22 or 31 wherein the ShK is modified by substitution of the Met residue at position 21.

38. A method according to claim 37 wherein the substitution at Met residue 21 deters oxidation.

39. A method according to claim 22 or 31 wherein the ShK is modified by substitution of the of the C-terminal acid function with an amide.

40. A method according to claim 39 wherein the substitution of the C-tenninal acid function with an amide imparts stability to C-terminal carboxypeptidase enzymes.

* * * * *

SEQUENCE LISTING

```
<160> NUMBER OF SEQ ID NOS: 4

<210> SEQ ID NO 1
<211> LENGTH: 35
<212> TYPE: PRT
<213> ORGANISM: Stichodactyla helianthus

<400> SEQUENCE: 1

Arg Ser Cys Ile Asp Thr Ile Pro Lys Ser Arg Cys Thr Ala Phe Gln
1               5                   10                  15

Cys Lys His Ser Met Lys Tyr Arg Leu Ser Phe Cys Arg Lys Thr Cys
            20                  25                  30

Gly Thr Cys
        35

<210> SEQ ID NO 2
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: p-phospho-Tyr
<220> FEATURE:
<221> NAME/KEY: MOD_RES
<222> LOCATION: (2)..(2)
<223> OTHER INFORMATION: AEEAc
```

```
<400> SEQUENCE: 2

Tyr Xaa Arg Ser Cys Ile Asp Thr Ile Pro Lys Ser Arg Cys Thr Ala
1               5                   10                  15

Phe Gln Cys Lys His Ser Met Lys Tyr Arg Leu Ser Phe Cys Arg Lys
            20                  25                  30

Thr Cys Gly Thr Cys
            35

<210> SEQ ID NO 3
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: p-phospho-Tyr
<220> FEATURE:
<221> NAME/KEY: MOD_RES
<222> LOCATION: (2)..(2)
<223> OTHER INFORMATION: AEEAc
<220> FEATURE:
<221> NAME/KEY: misc_feature
<222> LOCATION: (37)..(37)
<223> OTHER INFORMATION: C-term amidated

<400> SEQUENCE: 3

Tyr Xaa Arg Ser Cys Ile Asp Thr Ile Pro Lys Ser Arg Cys Thr Ala
1               5                   10                  15

Phe Gln Cys Lys His Ser Met Lys Tyr Arg Leu Ser Phe Cys Arg Lys
            20                  25                  30

Thr Cys Gly Thr Cys
            35

<210> SEQ ID NO 4
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: AEEAc
<220> FEATURE:
<221> NAME/KEY: misc_feature
<222> LOCATION: (37)..(37)
<223> OTHER INFORMATION: C-term amidated

<400> SEQUENCE: 4

Tyr Xaa Arg Ser Cys Ile Asp Thr Ile Pro Lys Ser Arg Cys Thr Ala
1               5                   10                  15

Phe Gln Cys Lys His Ser Met Lys Tyr Arg Leu Ser Phe Cys Arg Lys
            20                  25                  30

Thr Cys Gly Thr Cys
            35
```